(12) United States Patent
Lockwood et al.

(10) Patent No.: US 10,357,404 B2
(45) Date of Patent: *Jul. 23, 2019

(54) VACUUM THERAPY AND CLEANSING DRESSING FOR WOUNDS

(75) Inventors: Jeffrey S. Lockwood, Batesville, IN (US); Robert Petrosenko, Batesville, IN (US); James R. Risk, Jr., Fountaintown, IN (US)

(73) Assignee: KCI Medical Resources Unlimited Company, Grand Cayman (KY)

( * ) Notice: Subject to any disclaimer, the term of this patent is extended or adjusted under 35 U.S.C. 154(b) by 97 days.

This patent is subject to a terminal disclaimer.

(21) Appl. No.: 13/177,438

(22) Filed: Jul. 6, 2011

(65) Prior Publication Data

US 2011/0313374 A1    Dec. 22, 2011

Related U.S. Application Data

(63) Continuation of application No. 11/051,283, filed on Feb. 4, 2005, now Pat. No. 7,988,680, which is a (Continued)

(51) Int. Cl.
*A61M 35/00* (2006.01)
*A61M 1/00* (2006.01)
(Continued)

(52) U.S. Cl.
CPC ..... *A61F 13/00068* (2013.01); *A61M 1/0058* (2013.01); *A61M 1/0088* (2013.01);
(Continued)

(58) Field of Classification Search
CPC .......... A61M 35/00; A61M 1/00; A61M 3/00; A61M 31/00; A61F 13/00; A61F 13/02; A61F 8/44
(Continued)

(56) References Cited

U.S. PATENT DOCUMENTS 765,746 A    7/1904   Miner
774,529 A   11/1904   Nieschang ................. 601/14
(Continued)

FOREIGN PATENT DOCUMENTS

AU    550575    8/1982
AU    745271    4/1999
(Continued)

OTHER PUBLICATIONS

US 6,216,701 B1, 04/2001, Heaton et al. (withdrawn)
(Continued)

*Primary Examiner* — Tatyana Zalukaeva
*Assistant Examiner* — Ilya Y Treyger

(57) ABSTRACT

A wound dressing member is provided for use in a vacuum bandage connected to a vacuum source. The wound dressing member is also provided for use with a wound having a wound surface. The wound dressing member includes a wound facing surface adapted to be in contact with and generally conform to the wound surface and a plurality of discrete holes formed in the wound facing surface. The member further includes a port configured to communicate with the vacuum source and with each hole formed in the wound facing surface. The wound dressing member further includes a stand-off having interconnected portions coupled to the wound facing surface and configured to provide a space between the wound facing surface and the wound surface.

16 Claims, 20 Drawing Sheets

Related U.S. Application Data continuation of application No. 10/144,504, filed on May 13, 2002, now Pat. No. 6,855,135, which is a continuation-in-part of application No. 09/994,537, filed on Nov. 27, 2001, now Pat. No. 6,752,794, which is a continuation-in-part of application No. 09/725,352, filed on Nov. 29, 2000, now Pat. No. 6,685,681.

(51) Int. Cl.
*A61F 13/00* (2006.01)
*A61M 27/00* (2006.01)
*A61M 3/00* (2006.01)
*A61M 31/00* (2006.01)
*A61F 13/02* (2006.01)

(52) U.S. Cl.
CPC ... *A61M 27/00* (2013.01); *A61F 2013/00174* (2013.01); *A61F 2013/00536* (2013.01); *A61M 1/008* (2013.01); *A61M 1/0062* (2013.01)

(58) Field of Classification Search
USPC .......................................... 604/313, 315–318
See application file for complete search history.

(56) References Cited

U.S. PATENT DOCUMENTS

| | | | |
|---|---|---|---|
| 1,000,001 A | 8/1911 | Holz | 601/6 |
| 1,355,846 A | 10/1920 | Rannells | 604/286 |
| 1,385,346 A | 7/1921 | Taylor | 604/305 |
| 1,709,520 A | 4/1929 | Chandler | 292/259 R |
| 1,936,129 A | 11/1933 | Fisk | 604/313 |
| 2,078,180 A | 4/1937 | Kronenberg | 604/28 |
| 2,195,771 A | 4/1940 | Estler | 604/355 |
| 2,221,758 A | 11/1940 | Elmquist | 128/888 |
| 2,305,289 A | 12/1942 | Coburg | 128/132 |
| 2,338,339 A | 1/1944 | LaMere et al. | 601/7 |
| 2,443,481 A | 6/1948 | Sene | 128/88 |
| 2,547,758 A | 4/1951 | Keeling | 128/349 |
| 2,560,915 A | 7/1951 | Bamberger | 128/350 |
| 2,573,791 A | 11/1951 | Howells | 602/14 |
| 2,577,945 A | 12/1951 | Altherton | 602/1 |
| 2,632,443 A | 3/1953 | Lesher | 128/888 |
| 2,682,873 A | 7/1954 | Evans et al. | 602/42 |
| 2,910,763 A | 11/1959 | Lauterbach | 128/72.2 |
| 2,969,057 A | 1/1961 | Simmons | 128/2 |
| 3,026,874 A | 3/1962 | Stevens | 604/305 |
| 3,066,672 A | 12/1962 | Crosby, Jr. | 128/276 |
| 3,315,665 A | 4/1967 | MacLeod | 601/7 |
| 3,367,332 A | 2/1968 | Groves | 604/290 |
| 3,382,867 A | 5/1968 | Reaves | 601/7 |
| 3,430,631 A | 3/1969 | Abramson | 128/350 |
| 3,492,991 A | 2/1970 | Dryer | 604/6.09 |
| 3,520,300 A | 7/1970 | Flower et al. | 604/269 |
| 3,528,416 A | 9/1970 | Chamberlain | 128/888 |
| 3,568,675 A | 3/1971 | Harvey | 604/355 |
| 3,585,742 A | 6/1971 | Tyler | 40/642.02 |
| 3,599,639 A | 8/1971 | Spotz | 604/119 |
| 3,610,238 A | 10/1971 | Rich, Jr. | 604/23 |
| 3,623,087 A | 11/1971 | Gallichotte | 340/509 |
| 3,626,087 A | 12/1971 | Tomioka | 178/5.4 |
| 3,648,692 A | 3/1972 | Wheeler | 602/46 |
| 3,682,180 A | 8/1972 | McFarlane | 128/350 |
| 3,683,894 A | 8/1972 | Villari | 600/580 |
| 3,721,244 A | 3/1973 | Elmaleh | 604/128 |
| 3,752,158 A | 8/1973 | Kariher | 604/133 |
| 3,753,439 A | 8/1973 | Brugarolas et al. | 128/350 |
| 3,782,377 A | 1/1974 | Rychlik | 128/888 |
| 3,812,972 A | 5/1974 | Rosenblum | 210/489 |
| 3,814,095 A | 6/1974 | Lubens | 604/307 |
| 3,817,145 A | 6/1974 | Cohen | 84/471 |
| 3,823,720 A | 7/1974 | Tribble | 128/350 |
| 3,826,254 A | 7/1974 | Mellor | 128/133 |
| 3,831,588 A | 8/1974 | Rindner | 600/488 |
| 3,860,008 A | 1/1975 | Miner et al. | 128/350 |
| 3,874,387 A | 4/1975 | Barbieri | 602/53 |
| 3,903,882 A | 9/1975 | Augurt | 602/43 |
| 3,924,624 A | 12/1975 | Schachet | 128/276 |
| 3,935,863 A | 2/1976 | Kliger | 604/369 |
| 3,954,105 A | 5/1976 | Nordby et al. | 604/355 |
| 3,982,546 A | 9/1976 | Friend | 604/249 |
| 4,004,590 A | 1/1977 | Muriot | 604/326 |
| 4,013,076 A | 3/1977 | Puderbaugh et al. | 604/320 |
| RE29,319 E | 7/1977 | Nordby et al. | 604/355 |
| RE29,321 E | 7/1977 | Holbrook | 215/309 |
| 4,058,123 A | 11/1977 | May | 128/278 |
| 4,080,970 A | 3/1978 | Miller | 604/174 |
| 4,096,853 A | 6/1978 | Weigand | 128/2 |
| 4,112,947 A | 9/1978 | Nehring | 604/30 |
| 4,139,004 A | 2/1979 | Gonzalez, Jr. | 602/14 |
| 4,149,541 A | 4/1979 | Gammons et al. | 607/104 |
| 4,165,748 A | 8/1979 | Johnson | 128/348 |
| 4,178,974 A | 12/1979 | Levin | 141/51 |
| 4,184,510 A | 1/1980 | Murry | 137/565 |
| 4,191,204 A | 3/1980 | Nehring | 137/205 |
| 4,219,021 A | 8/1980 | Fink | 128/214 |
| 4,224,941 A | 9/1980 | Stivala | 604/23 |
| 4,233,969 A | 11/1980 | Lock | 128/156 |
| 4,245,630 A | 1/1981 | Lloyd | 128/155 |
| 4,250,882 A | 2/1981 | Adair | 604/355 |
| 4,256,109 A | 3/1981 | Nichols | 128/276 |
| 4,261,363 A | 4/1981 | Russo | 128/350 |
| 4,275,721 A | 6/1981 | Olson | 604/180 |
| 4,284,079 A | 8/1981 | Adair | 128/295 |
| 4,297,995 A | 11/1981 | Golub | 604/304 |
| 4,333,468 A | 6/1982 | Geist | 128/348 |
| 4,341,209 A | 7/1982 | Schaar | 602/58 |
| 4,364,394 A | 12/1982 | Wilkinson | 604/96 |
| 4,373,519 A | 2/1983 | Errede et al. | 602/43 |
| 4,382,441 A | 5/1983 | Svedman | 604/291 |
| 4,392,853 A | 7/1983 | Muto | 604/171 |
| 4,392,858 A | 7/1983 | George et al. | 604/187 |
| 4,399,816 A | 8/1983 | Spangler | 128/888 |
| 4,419,097 A | 12/1983 | Rowland | 604/174 |
| 4,445,897 A | 5/1984 | Ekbladh | 604/280 |
| 4,457,755 A | 7/1984 | Wilson | 604/184 |
| 4,460,370 A | 7/1984 | Allison et al. | 424/448 |
| 4,465,062 A | 8/1984 | Versaggi et al. | 128/897 |
| 4,465,485 A | 8/1984 | Kashmer et al. | 604/320 |
| 4,469,092 A | 9/1984 | Marshall et al. | 601/70 |
| 4,475,909 A | 10/1984 | Eisenberg | 604/349 |
| 4,480,638 A | 11/1984 | Schmid | 128/155 |
| 4,508,533 A | 4/1985 | Abramson | 604/35 |
| 4,523,920 A | 6/1985 | Russo | |
| 4,525,156 A | 6/1985 | Benusa et al. | 604/28 |
| 4,525,166 A | 6/1985 | Leclerc | 604/133 |
| 4,525,374 A | 6/1985 | Vaillancourt | 427/2 |
| 4,533,352 A | 8/1985 | Van Beek et al. | 604/317 |
| 4,533,419 A | 8/1985 | Pieslak et al. | 156/85 |
| 4,540,412 A | 9/1985 | Van Overloop | 604/291 |
| 4,543,100 A | 9/1985 | Brodsky | 604/180 |
| 4,548,202 A | 10/1985 | Duncan | 128/334 |
| 4,551,139 A | 11/1985 | Plaas et al. | 604/290 |
| 4,553,967 A | 11/1985 | Ferguson et al. | 604/317 |
| 4,569,348 A | 2/1986 | Hasslinger | 604/179 |
| 4,569,674 A | 2/1986 | Phillips et al. | 604/119 |
| 4,573,965 A | 3/1986 | Russo | 604/30 |
| 4,579,555 A | 4/1986 | Russo | 604/541 |
| 4,596,564 A | 6/1986 | Spetzler | 604/281 |
| 4,605,399 A | 8/1986 | Weston et al. | 604/305 |
| 4,608,041 A | 8/1986 | Nielsen | 604/23 |
| 4,614,794 A | 9/1986 | Easton | 530/356 |
| 4,624,656 A | 11/1986 | Clark et al. | 604/23 |
| 4,633,863 A | 1/1987 | Filips et al. | 128/846 |
| 4,637,819 A | 1/1987 | Ouellette et al. | 604/369 |
| 4,640,688 A | 2/1987 | Hauser | 604/352 |
| 4,641,643 A | 2/1987 | Greer | 128/888 |
| 4,645,492 A | 2/1987 | Weeks | 604/174 |
| 4,655,210 A | 4/1987 | Edenbaum et al. | 602/46 |
| 4,655,754 A | 4/1987 | Richmond et al. | 604/323 |
| 4,661,093 A | 4/1987 | Beck et al. | 604/543 |
| 4,664,652 A | 5/1987 | Weilbacher | 604/133 |

(56) References Cited

U.S. PATENT DOCUMENTS

| | | | |
|---|---|---|---|
| 4,664,662 A | 5/1987 | Webster | 602/47 |
| 4,667,666 A | 5/1987 | Frysliie | 128/888 |
| 4,679,590 A | 7/1987 | Hergenroeer | 137/602 |
| 4,704,102 A | 11/1987 | Guthery | 604/28 |
| 4,710,165 A | 12/1987 | McNeil | 604/67 |
| 4,713,051 A | 12/1987 | Steppe et al. | 604/30 |
| 4,717,332 A | 1/1988 | Edens | 431/8 |
| 4,717,379 A | 1/1988 | Ekholmer | 604/43 |
| 4,717,382 A | 1/1988 | Clemens et al. | 604/122 |
| 4,728,323 A | 3/1988 | Matson | 604/304 |
| 4,733,659 A | 3/1988 | Edenbaum et al. | 602/54 |
| 4,735,606 A | 4/1988 | Davison | 604/28 |
| 4,735,610 A | 4/1988 | Akkas et al. | 604/119 |
| 4,737,148 A | 4/1988 | Blake | 604/126 |
| 4,743,232 A | 5/1988 | Kruger | 604/180 |
| 4,747,166 A | 5/1988 | Kuntz | 4/144.1 |
| 4,758,220 A | 7/1988 | Sundblom | 604/65 |
| 4,759,354 A | 7/1988 | Quarfoot | 602/50 |
| 4,740,202 A | 8/1988 | Stacey et al. | 604/119 |
| 4,765,316 A | 8/1988 | Marshall | 601/70 |
| 4,778,446 A | 10/1988 | Jensen | 604/27 |
| 4,778,456 A | 10/1988 | Lokken | 604/290 |
| 4,787,888 A | 11/1988 | Fox | 604/20 |
| 4,795,428 A | 1/1989 | Hwang | 604/73 |
| 4,798,578 A | 1/1989 | Ranford | 604/6.09 |
| 4,820,265 A | 4/1989 | DeSatnick et al. | 604/30 |
| 4,820,284 A | 4/1989 | Hauri | 604/318 |
| 4,826,494 A | 5/1989 | Richmond et al. | 604/323 |
| 4,826,949 A | 5/1989 | Stanko | 528/272 |
| 4,834,110 A | 5/1989 | Richard | 600/573 |
| 4,838,883 A | 6/1989 | Matsuura | 604/349 |
| 4,840,187 A | 6/1989 | Brazier | 128/844 |
| 4,841,962 A | 6/1989 | Berg et al. | 128/156 |
| 4,850,350 A | 7/1989 | Jackson | 128/207.16 |
| 4,863,449 A | 9/1989 | Therriault et al. | 604/352 |
| 4,872,450 A | 10/1989 | Austard | 602/48 |
| 4,878,901 A | 11/1989 | Sachse | 604/174 |
| 4,890,608 A | 1/1990 | Steer | 602/57 |
| 4,897,081 A | 1/1990 | Poirer et al. | 604/175 |
| 4,900,302 A | 2/1990 | Newton | 604/30 |
| 4,902,508 A | 2/1990 | Badylak et al. | 424/95 |
| 4,906,233 A | 3/1990 | Moriuchi et al. | 604/174 |
| 4,906,240 A | 3/1990 | Reed et al. | 604/307 |
| 4,915,694 A | 4/1990 | Yamamoto et al. | 604/180 |
| 4,917,112 A | 4/1990 | Kalt | 602/58 |
| 4,919,654 A | 4/1990 | Kalt | 604/180 |
| 4,921,492 A | 5/1990 | Schultz et al. | 604/315 |
| 4,930,997 A | 6/1990 | Bennett | 471/410 |
| 4,941,882 A | 7/1990 | Ward et al. | 604/180 |
| 4,950,230 A | 8/1990 | Kendell | 604/28 |
| 4,953,565 A | 9/1990 | Tachibana et al. | 607/152 |
| 4,956,178 A | 9/1990 | Badylak | 424/551 |
| 4,957,492 A | 9/1990 | McVay | 604/319 |
| 4,962,761 A | 10/1990 | Golden | 607/104 |
| 4,969,880 A | 11/1990 | Zamierowski | 604/305 |
| 4,969,881 A | 11/1990 | Viesturs | 604/305 |
| 4,970,298 A | 11/1990 | Silver et al. | 530/356 |
| 4,985,019 A | 1/1991 | Michelson | 604/180 |
| 4,988,336 A | 1/1991 | Kohn | 604/67 |
| 4,990,144 A | 2/1991 | Blott | 604/304 |
| 4,991,574 A | 2/1991 | Pocknell | 602/48 |
| 4,994,022 A | 2/1991 | Steffler et al. | 604/7 |
| 4,997,425 A | 3/1991 | Shioya et al. | 604/304 |
| 5,000,172 A | 3/1991 | Ward | 128/155 |
| 5,000,741 A | 3/1991 | Kalt | 604/180 |
| 5,002,528 A | 3/1991 | Palestrant | 604/28 |
| 5,002,529 A | 3/1991 | Cunningham | 604/73 |
| 5,003,971 A | 4/1991 | Buckley | 602/54 |
| 5,014,389 A | 5/1991 | Ogilvie et al. | 15/353 |
| 5,034,003 A | 7/1991 | Denance | 604/117 |
| 5,034,006 A | 7/1991 | Hosoda et al. | 604/317 |
| 5,035,865 A | 7/1991 | Inaba et al. | 422/99 |
| 5,037,397 A | 8/1991 | Kalt | 604/174 |
| 5,042,978 A | 8/1991 | Quenin et al. | 604/317 |
| 5,045,777 A | 9/1991 | Itagaki | 324/76.12 |
| 5,060,662 A | 10/1991 | Farnsworth, III | 128/888 |
| 5,069,907 A | 12/1991 | Mixon et al. | 424/445 |
| 5,071,409 A | 12/1991 | Rosenberg | 604/119 |
| 5,073,172 A | 12/1991 | Fell | 604/319 |
| 5,080,650 A | 1/1992 | Hirsch et al. | 604/104 |
| 5,086,170 A | 2/1992 | Luheshi et al. | 540/303 |
| 5,086,763 A | 2/1992 | Hathman | 602/42 |
| 5,086,764 A | 2/1992 | Gilman | 602/42 |
| 5,092,858 A | 3/1992 | Benson et al. | 604/319 |
| 5,100,395 A | 3/1992 | Rosenberg | 604/284 |
| 5,100,396 A | 3/1992 | Zamierowski | 604/305 |
| 5,101,808 A | 4/1992 | Kobayashi et al. | 601/44 |
| 5,106,362 A | 4/1992 | Gilman | 602/47 |
| 5,106,629 A | 4/1992 | Cartmell et al. | 424/445 |
| 5,108,364 A | 4/1992 | Takezawa et al. | 604/43 |
| 5,116,310 A | 5/1992 | Seder et al. | |
| 5,134,994 A | 8/1992 | Say | 128/200.24 |
| 5,135,518 A | 8/1992 | Vera | 604/291 |
| 5,146,925 A | 9/1992 | Snow | 600/435 |
| 5,147,338 A | 9/1992 | Lang et al. | 604/304 |
| 5,149,331 A | 9/1992 | Ferdman et al. | 604/290 |
| 5,152,757 A | 10/1992 | Erikson | 604/305 |
| 5,160,322 A | 11/1992 | Scheremet et al. | 604/122 |
| 5,167,613 A | 12/1992 | Karami et al. | 602/42 |
| 5,167,622 A | 12/1992 | Muto | 604/35 |
| 5,170,781 A | 12/1992 | Loomis | 128/118.1 |
| 5,176,502 A | 1/1993 | Sanderson et al. | 417/18 |
| 5,176,663 A | 1/1993 | Svedman et al. | 604/305 |
| 5,176,667 A | 1/1993 | DeBring | 604/356 |
| 5,181,908 A | 1/1993 | Bell | 604/24 |
| 5,189,609 A | 2/1993 | Tivig et al. | 600/300 |
| 5,197,948 A | 3/1993 | Ghodsian | 604/30 |
| 5,215,522 A | 6/1993 | Page | 604/33 |
| 5,215,539 A | 6/1993 | Schoolman | 604/541 |
| 5,224,929 A | 7/1993 | Remiszewski | 604/30 |
| 5,228,431 A | 7/1993 | Giarretto | 601/9 |
| 5,230,350 A | 7/1993 | Fentress | 128/846 |
| 5,232,453 A | 8/1993 | Plass | 604/180 |
| 5,238,654 A | 8/1993 | Nohl et al. | 422/100 |
| 5,249,121 A | 9/1993 | Baum et al. | 606/1 |
| 5,256,418 A | 10/1993 | Kemp et al. | 424/423 |
| 5,261,893 A | 11/1993 | Zamierowski | 604/180 |
| 5,263,922 A | 11/1993 | Soya et al. | 602/59 |
| 5,265,605 A | 11/1993 | Afflerbach | 600/300 |
| 5,275,826 A | 1/1994 | Badylak et al. | 424/551 |
| 5,278,100 A | 1/1994 | Doan | 437/200 |
| 5,279,550 A | 1/1994 | Habib et al. | 604/38 |
| 5,281,422 A | 1/1994 | Badylak et al. | 424/551 |
| 5,291,887 A | 3/1994 | Stanley et al. | 600/529 |
| 5,298,015 A | 3/1994 | Komatsuzaki et al. | 602/46 |
| 5,306,298 A | 4/1994 | Godley, III et al. | 623/9 |
| 5,314,409 A | 5/1994 | Sarosiek et al. | 604/101 |
| 5,330,452 A | 7/1994 | Zook | 604/307 |
| 5,335,651 A | 8/1994 | Foster | 128/202.13 |
| 5,338,293 A | 8/1994 | Jeppsson et al. | 604/29 |
| 5,342,293 A | 8/1994 | Zanger | 604/22 |
| 5,342,301 A | 8/1994 | Saab | 604/96 |
| 5,342,376 A | 8/1994 | Ruff | 606/151 |
| 5,344,415 A | 9/1994 | DeBusk et al. | 604/304 |
| 5,349,965 A | 9/1994 | McCarver | 128/846 |
| 5,352,463 A | 10/1994 | Badylak et al. | 424/551 |
| 5,358,494 A | 10/1994 | Svedman | 604/313 |
| 5,370,610 A | 12/1994 | Reynolds | 604/43 |
| 5,372,821 A | 12/1994 | Badylak et al. | 424/551 |
| 5,374,254 A | 12/1994 | Burma | 604/175 |
| 5,376,252 A | 12/1994 | Eckstrom et al. | 204/603 |
| 5,380,280 A | 1/1995 | Peterson | 604/65 |
| 5,395,315 A | 3/1995 | Griep | 604/35 |
| 5,409,013 A | 4/1995 | Clement | 128/753 |
| 5,413,788 A | 5/1995 | Edwards et al. | 424/409 |
| 5,419,768 A | 5/1995 | Kayser | 604/119 |
| 5,431,622 A | 7/1995 | Pyrozyk et al. | 602/2 |
| 5,437,622 A | 8/1995 | Carton | 602/57 |
| 5,437,651 A | 8/1995 | Todd et al. | 604/313 |
| 5,439,452 A | 8/1995 | McCarty | 604/248 |
| 5,445,604 A | 8/1995 | Lang | 602/47 |
| 5,445,833 A | 8/1995 | Badylak et al. | 424/551 |
| 5,447,505 A | 9/1995 | Valentine et al. | 604/304 |
| 5,449,383 A | 9/1995 | Chatelier et al. | 623/1 |

(56) References Cited

U.S. PATENT DOCUMENTS

| | | | | |
|---|---|---|---|---|
| 5,451,215 | A | 9/1995 | Wolter | 604/265 |
| 5,451,373 | A | 9/1995 | Lewis et al. | 422/82.13 |
| 5,478,333 | A | 12/1995 | Asherman, Jr. | 604/304 |
| 5,484,420 | A | 1/1996 | Russo | 604/178 |
| 5,484,427 | A | 1/1996 | Gibbons | 604/313 |
| 5,484,428 | A | 1/1996 | Drainville et al. | 604/319 |
| 5,487,889 | A | 1/1996 | Eckert et al. | 424/93.1 |
| 5,516,533 | A | 5/1996 | Badylak et al. | 424/551 |
| 5,520,652 | A | 5/1996 | Peterson | 604/119 |
| 5,527,293 | A | 6/1996 | Zamierowski | 604/176 |
| 5,531,670 | A | 7/1996 | Westby et al. | 602/41 |
| 5,533,981 | A | 7/1996 | Mandro et al. | 604/208 |
| 5,534,346 | A | 7/1996 | Robinson | 428/343 |
| 5,540,668 | A | 7/1996 | Wilson | 604/248 |
| 5,542,918 | A | 8/1996 | Atkinson | 604/27 |
| 5,549,584 | A | 8/1996 | Gross | 604/313 |
| 5,554,389 | A | 9/1996 | Badylak et al. | 424/558 |
| 5,556,375 | A | 9/1996 | Ewall | 602/58 |
| 5,558,639 | A | 9/1996 | Gangemi | 604/67 |
| 5,573,784 | A | 11/1996 | Badylak et al. | 424/551 |
| 5,578,022 | A | 11/1996 | Scherson et al. | 604/304 |
| 5,578,662 | A | 11/1996 | Bennett et al. | 524/144 |
| 5,607,388 | A | 3/1997 | Ewall | 602/58 |
| 5,607,683 | A | 3/1997 | Capelli | 424/405 |
| 5,616,338 | A | 4/1997 | Fox et al. | 424/423 |
| 5,621,035 | A | 4/1997 | Lyles | 524/404 |
| 5,624,417 | A | 4/1997 | Cook | 604/319 |
| 5,624,418 | A | 4/1997 | Shepard | 604/319 |
| 5,628,735 | A | 5/1997 | Skow | 604/317 |
| 5,629,186 | A | 5/1997 | Yasukawa et al. | 435/177 |
| 5,631,011 | A | 5/1997 | Wadström | 424/400 |
| 5,635,201 | A | 6/1997 | Fabo | 424/443 |
| 5,636,643 | A * | 6/1997 | Argenta et al. | 128/897 |
| 5,641,518 | A | 6/1997 | Badylak | 424/551 |
| 5,645,081 | A | 7/1997 | Argenta et al. | 128/897 |
| 5,645,860 | A | 7/1997 | Knapp et al. | 424/551 |
| 5,655,258 | A | 8/1997 | Heintz | 15/415.1 |
| 5,656,027 | A | 8/1997 | Ellingboe | 604/541 |
| 5,662,598 | A | 9/1997 | Tobin | 602/41 |
| 5,662,624 | A | 9/1997 | Sundstrom et al. | 604/291 |
| 5,662,625 | A | 9/1997 | Westwood | 604/305 |
| 5,669,892 | A | 9/1997 | Keogh et al. | 604/320 |
| 5,672,151 | A | 9/1997 | Calderon-Garcidueilas | 602/21 |
| 5,672,152 | A | 9/1997 | Mason et al. | 602/26 |
| 5,674,193 | A | 10/1997 | Hayes | 604/28 |
| 5,678,564 | A | 10/1997 | Lawrence et al. | 600/574 |
| 5,681,290 | A | 10/1997 | Alexander | 604/180 |
| 5,690,815 | A | 11/1997 | Krasnoff et al. | 210/97 |
| 5,695,998 | A | 12/1997 | Badylak et al. | 435/391 |
| 5,697,920 | A | 12/1997 | Gibbons | 604/289 |
| 5,711,969 | A | 1/1998 | Patel et al. | 424/551 |
| 5,718,955 | A | 2/1998 | McGuire et al. | 428/35.7 |
| 5,735,833 | A | 4/1998 | Olson | 604/289 |
| 5,738,656 | A | 4/1998 | Wagner | 604/119 |
| 5,741,237 | A | 4/1998 | Walker | 604/317 |
| 5,749,842 | A | 5/1998 | Cheong | 602/41 |
| 5,753,267 | A | 5/1998 | Badylak | 424/551 |
| 5,755,791 | A | 5/1998 | Whitson et al. | 623/15 |
| 5,759,570 | A | 6/1998 | Arnold | 424/443 |
| 5,762,640 | A | 6/1998 | Kajiwara et al. | 604/313 |
| 5,762,966 | A | 6/1998 | Knapp et al. | 424/551 |
| 5,780,281 | A | 7/1998 | Yasukawa et al. | 435/176 |
| 5,782,871 | A | 7/1998 | Fujiwara et al. | 604/313 |
| 5,795,584 | A | 8/1998 | Totakura et al. | 424/426 |
| 5,800,383 | A | 9/1998 | Chandler et al. | 604/35 |
| 5,817,145 | A | 10/1998 | Augustine et al. | 607/96 |
| 5,827,246 | A | 10/1998 | Bowen | 604/313 |
| 5,827,296 | A | 10/1998 | Morris et al. | 606/129 |
| 5,855,619 | A | 1/1999 | Caplan et al. | 623/11 |
| 5,866,414 | A | 2/1999 | Badylak et al. | 435/325 |
| 5,881,723 | A | 3/1999 | Wallace et al. | 128/204.21 |
| 5,891,111 | A | 4/1999 | Ismael | 604/280 |
| 5,902,874 | A | 5/1999 | Roby | 528/310 |
| 5,902,875 | A | 5/1999 | Roby | 528/310 |
| 5,911,222 | A | 6/1999 | Lawrence et al. | 600/574 |
| 5,914,387 | A | 6/1999 | Roby | 528/310 |
| 5,919,476 | A | 7/1999 | Fischer et al. | 424/443 |
| 5,921,972 | A | 7/1999 | Skow | 604/313 |
| 5,928,174 | A | 7/1999 | Gibbins | 602/41 |
| 5,931,304 | A | 8/1999 | Hammond | 206/570 |
| 5,941,859 | A | 8/1999 | Lerman | 604/289 |
| 5,942,496 | A | 8/1999 | Bonadio | 514/44 |
| 5,947,914 | A | 9/1999 | Augustine | 602/2 |
| 5,951,295 | A | 9/1999 | Lyles | 433/228.1 |
| 5,954,680 | A | 9/1999 | Augustine | 602/42 |
| 5,961,480 | A | 10/1999 | Augustine | 602/41 |
| 5,962,427 | A | 10/1999 | Goldstein | 514/44 |
| 5,964,721 | A | 10/1999 | Augustine | 602/2 |
| 5,964,723 | A | 10/1999 | Augustine | 602/42 |
| 5,986,163 | A | 11/1999 | Augustine | 602/42 |
| 5,997,568 | A | 12/1999 | Liu | 606/228 |
| 6,010,527 | A | 1/2000 | Augustine et al. | 607/96 |
| 6,013,048 | A | 1/2000 | Podany | 604/22 |
| 6,013,097 | A * | 1/2000 | Augustine et al. | 607/96 |
| 6,017,493 | A | 1/2000 | Cambron et al. | 422/44 |
| 6,039,724 | A | 3/2000 | Seifert et al. | 604/533 |
| 6,045,518 | A | 4/2000 | Augustine | 602/2 |
| 6,045,541 | A | 4/2000 | Matsumoto et al. | 604/313 |
| 6,051,747 | A | 4/2000 | Lindqvist | 602/46 |
| 6,056,730 | A | 5/2000 | Greter | 604/319 |
| 6,071,254 | A | 6/2000 | Augustine | 602/2 |
| 6,071,267 | A | 6/2000 | Zamierowski | 604/289 |
| 6,071,304 | A | 6/2000 | Augustine et al. | 607/96 |
| 6,080,189 | A | 6/2000 | Augustine et al. | 607/96 |
| 6,080,243 | A | 6/2000 | Insley et al. | 134/21 |
| 6,093,160 | A | 7/2000 | Augustine et al. | 602/2 |
| 6,093,230 | A | 7/2000 | Johnson et al. | 55/482 |
| 6,095,992 | A | 8/2000 | Augustine et al. | 602/2 |
| 6,099,567 | A | 8/2000 | Badylak et al. | 623/13 |
| 6,110,197 | A | 8/2000 | Augustine | 607/108 |
| 6,113,561 | A | 9/2000 | Augustine | 602/2 |
| 6,117,111 | A | 9/2000 | Fleischmann | 604/180 |
| 6,135,116 | A | 10/2000 | Vogel et al. | 128/898 |
| 6,142,982 | A | 11/2000 | Hunt et al. | 604/313 |
| 6,143,945 | A | 11/2000 | Augustine et al. | 602/41 |
| 6,149,614 | A | 11/2000 | Dunshee et al. | 602/57 |
| 6,171,344 | B1 | 1/2001 | Atala | 623/23.64 |
| 6,174,306 | B1 | 1/2001 | Fleischmann | 604/543 |
| 6,203,563 | B1 | 3/2001 | Fernandez | 606/215 |
| 6,206,931 | B1 | 3/2001 | Cook et al. | 623/23.75 |
| 6,207,875 | B1 | 3/2001 | Lindqvist et al. | 602/46 |
| 6,213,965 | B1 | 4/2001 | Augustine et al. | 602/2 |
| 6,213,966 | B1 | 4/2001 | Augustine | 602/2 |
| 6,217,535 | B1 | 4/2001 | Augustine | 602/2 |
| 6,235,009 | B1 | 5/2001 | Skow | 604/317 |
| 6,235,047 | B1 | 5/2001 | Augustine et al. | 607/96 |
| 6,241,697 | B1 | 6/2001 | Augustine | 602/2 |
| 6,241,698 | B1 | 6/2001 | Augustine | 602/2 |
| 6,241,747 | B1 | 6/2001 | Ruff | 606/216 |
| 6,244,311 | B1 | 6/2001 | Hand et al. | 141/375 |
| 6,248,084 | B1 | 6/2001 | Augustine et al. | 602/2 |
| 6,254,557 | B1 | 7/2001 | Augustine et al. | 602/2 |
| 6,254,580 | B1 | 7/2001 | Svedman | 604/313 |
| 6,259,067 | B1 | 7/2001 | Faries, Jr. et al. | 219/428 |
| 6,264,622 | B1 | 7/2001 | Augustine | 602/2 |
| 6,264,979 | B1 | 7/2001 | Svedman | 424/449 |
| 6,267,740 | B1 | 7/2001 | Augustine | 602/2 |
| 6,283,931 | B1 | 9/2001 | Augustine | 602/2 |
| 6,284,941 | B1 | 9/2001 | Cox et al. | 602/48 |
| 6,287,316 | B1 | 9/2001 | Agarwal | 606/151 |
| 6,290,685 | B1 | 9/2001 | Insley et al. | 604/317 |
| 6,293,917 | B1 | 9/2001 | Augustine et al. | 602/2 |
| 6,325,798 | B1 | 12/2001 | Edwards et al. | 606/41 |
| 6,345,623 | B1 | 2/2002 | Heaton et al. | 128/897 |
| 6,364,853 | B1 | 4/2002 | French et al. | 604/35 |
| 6,394,142 | B1 | 5/2002 | Woelfel et al. | 138/115 |
| 6,398,767 | B1 | 6/2002 | Fleischmann | 604/313 |
| 6,410,427 | B1 | 6/2002 | Hu | 438/655 |
| 6,440,427 | B1 | 8/2002 | Wadström | 424/400 |
| 6,458,109 | B1 | 10/2002 | Henley et al. | 604/304 |
| 6,471,685 | B1 | 10/2002 | Johnson | 604/890.1 |
| 6,472,581 | B1 | 10/2002 | Muramatsu et al. | 602/41 |
| 6,491,693 | B1 | 10/2002 | Lytinaas | 606/53 |

(56) References Cited

U.S. PATENT DOCUMENTS

| | | | |
|---|---|---|---|
| 6,488,643 B1 | 12/2002 | Turney | 602/13 |
| 6,491,682 B2 | 12/2002 | Pademi | 604/541 |
| 6,493,568 B1 | 12/2002 | Bell | 600/323 |
| 6,500,112 B1 | 12/2002 | Khouri | 600/38 |
| 6,520,982 B1 | 2/2003 | Boynton et al. | 607/104 |
| 6,553,998 B2 | 4/2003 | Heaton et al. | 128/897 |
| 6,557,704 B1 | 5/2003 | Randolph | 206/363 |
| 6,559,773 B1 | 5/2003 | Berry | 340/815.4 |
| 6,599,277 B2 | 7/2003 | Neubert | 604/317 |
| 6,626,891 B2 | 9/2003 | Ohmstede | 604/543 |
| 6,638,270 B2 | 10/2003 | Johnson | 604/890.1 |
| 6,648,862 B2 | 11/2003 | Watson | 604/319 |
| 6,663,349 B1 | 12/2003 | Disenzo et al. | 417/44.1 |
| 6,685,681 B2 | 2/2004 | Lockwood et al. | 604/305 |
| 6,691,047 B1 | 2/2004 | Friedericks | 702/47 |
| 6,695,823 B1 | 2/2004 | Lina et al. | 604/304 |
| 6,695,824 B2 | 2/2004 | Howard et al. | 604/305 |
| 6,719,779 B2 | 4/2004 | Daoud | 607/105 |
| 6,749,592 B2 | 6/2004 | Lord | 604/319 |
| 6,752,794 B2 | 6/2004 | Lockwood et al. | 604/313 |
| 6,755,807 B2 | 6/2004 | Risk, Jr. et al. | 604/319 |
| 6,764,462 B2 | 7/2004 | Risk, Jr. et al. | 604/67 |
| 6,767,334 B1 | 7/2004 | Randolph | 604/35 |
| 6,775,807 B2 | 8/2004 | Lowther et al. | 604/319 |
| 6,794,554 B2 | 9/2004 | Sessions et al. | 602/46 |
| 6,800,074 B2 | 10/2004 | Henley et al. | 604/319 |
| 6,814,079 B2 | 11/2004 | Heaton et al. | 128/897 |
| 6,824,533 B2 | 11/2004 | Risk, Jr. et al. | 604/319 |
| 6,855,135 B2 | 2/2005 | Lockwood et al. | 604/313 |
| 6,856,821 B2 | 2/2005 | Johnson | 600/345 |
| 6,936,037 B2 | 8/2005 | Bubb et al. | 604/327 |
| 6,951,553 B2 | 10/2005 | Bubb et al. | 604/327 |
| 6,966,889 B2 | 11/2005 | Saab | 604/96.01 |
| 6,979,324 B2 | 12/2005 | Bybordi et al. | 604/313 |
| 6,994,702 B1 | 2/2006 | Johnson | 606/9 |
| 6,994,708 B2 | 2/2006 | Manzo | 606/45 |
| 7,004,915 B2 | 2/2006 | Boynton et al. | 601/6 |
| 7,022,113 B2 | 4/2006 | Lockwood et al. | 604/313 |
| 7,070,584 B2 | 7/2006 | Johnson et al. | 604/313 |
| 7,077,832 B2 | 7/2006 | Fleischmann | 604/304 |
| 7,108,683 B2 | 9/2006 | Zamierowski | 604/304 |
| 7,117,869 B2 | 10/2006 | Heaton et al. | 128/897 |
| 7,128,735 B2 | 10/2006 | Weston | 604/543 |
| 7,144,390 B1 | 12/2006 | Hannigan et al. | 604/313 |
| 7,195,624 B2 | 3/2007 | Lockwood et al. | 604/543 |
| 7,216,651 B2 | 5/2007 | Argenta et al. | 128/897 |
| 7,245,291 B2 | 7/2007 | Sharif et al. | 345/172 |
| 7,273,054 B2 | 9/2007 | Heaton et al. | 128/897 |
| 7,276,051 B1 | 10/2007 | Henley et al. | 604/304 |
| 7,338,482 B2 | 3/2008 | Lockwood et al. | 604/543 |
| 7,351,250 B2 | 4/2008 | Zamierowski | 606/215 |
| 7,381,211 B2 | 6/2008 | Zamierowski | 606/215 |
| 7,381,859 B2 | 6/2008 | Hunt | 602/46 |
| 7,410,495 B2 | 8/2008 | Zamierowski | 606/216 |
| 7,413,570 B2 | 8/2008 | Zamierowski | 606/215 |
| 7,413,571 B2 | 8/2008 | Zamierowski | 606/215 |
| 7,422,576 B2 | 9/2008 | Boynton et al. | 604/291 |
| 7,524,286 B2 | 4/2009 | Johnson | 600/309 |
| 7,534,927 B2 | 5/2009 | Lockwood et al. | 602/46 |
| 7,618,382 B2 | 11/2009 | Vogel et al. | 601/7 |
| 2001/0029956 A1 | 10/2001 | Argenta et al. | 128/897 |
| 2001/0034499 A1 | 10/2001 | Sessions | 602/46 |
| 2001/0043943 A1 | 11/2001 | Coffey | 424/447 |
| 2001/0052681 A1 | 12/2001 | Deavila | 280/47.19 |
| 2002/0065494 A1 | 5/2002 | Lockwood et al. | 604/313 |
| 2002/0077661 A1 | 6/2002 | Saadat | 606/221 |
| 2002/0082567 A1 | 6/2002 | Lockwood et al. | 604/313 |
| 2002/0082688 A1 | 6/2002 | Sander et al. | 623/2.13 |
| 2002/0085952 A1 | 7/2002 | Ellingboe et al. | 422/45 |
| 2002/0115951 A1 | 8/2002 | Norstrem | 602/27 |
| 2002/0115952 A1 | 8/2002 | Johnson et al. | 602/41 |
| 2002/0120185 A1 | 8/2002 | Johnson | 600/345 |
| 2002/0143286 A1 | 10/2002 | Tumey | 604/11 |
| 2002/0161317 A1 | 10/2002 | Risk et al. | 602/2 |
| 2002/0161346 A1 | 10/2002 | Lockwood et al. | 604/315 |
| 2002/0183702 A1 | 12/2002 | Henley et al. | 604/305 |
| 2002/0193723 A1 | 12/2002 | Batdorf et al. | 602/48 |
| 2003/0032951 A1 | 2/2003 | Rittman et al. | 606/34 |
| 2003/0077311 A1 | 4/2003 | Vyakarnam et al. | 435/41 |
| 2003/0093041 A1 | 5/2003 | Risk, Jr. et al. | 604/308 |
| 2003/0143352 A1 | 7/2003 | Yang et al. | 428/36.9 |
| 2003/0208149 A1 | 11/2003 | Coffey | 602/48 |
| 2003/0219469 A1 | 11/2003 | Johnson et al. | 424/445 |
| 2003/0225441 A1 | 12/2003 | Boyton | 607/104 |
| 2004/0030304 A1 | 2/2004 | Hunt et al. | 604/317 |
| 2004/0039415 A1 | 2/2004 | Zamierowski | 606/216 |
| 2004/0064111 A1 | 4/2004 | Lockwood et al. | 604/305 |
| 2004/0167482 A1 | 8/2004 | Watson | 604/317 |
| 2004/0225208 A1 | 11/2004 | Johnson | 600/364 |
| 2004/0243073 A1 | 12/2004 | Lockwood et al. | 604/313 |
| 2004/0249353 A1 | 12/2004 | Risks et al. | 604/315 |
| 2004/0260230 A1 | 12/2004 | Randolph | 604/28 |
| 2005/0004534 A1 | 1/2005 | Lockwood et al. | 604/304 |
| 2005/0010153 A1 | 1/2005 | Lockwood et al. | 602/41 |
| 2005/0033197 A1 | 2/2005 | Cottler | 600/573 |
| 2005/0065484 A1 | 3/2005 | Watson | 604/289 |
| 2005/0070858 A1 | 3/2005 | Lockwood et al. | 604/319 |
| 2005/0085795 A1 | 4/2005 | Lockwood et al. | 604/543 |
| 2005/0090787 A1 | 4/2005 | Risk et al. | 604/305 |
| 2005/0131327 A1 | 6/2005 | Lockwood et al. | 602/41 |
| 2005/0177190 A1 | 8/2005 | Zamierowski | 606/215 |
| 2005/0182445 A1 | 8/2005 | Zamierowski | 606/213 |
| 2005/0182446 A1 | 8/2005 | DeSantis | 606/222 |
| 2005/0234485 A1 | 10/2005 | Seegert et al. | 606/172 |
| 2005/0234510 A1 | 10/2005 | Zamierowski | 606/215 |
| 2005/0240220 A1 | 10/2005 | Zamierowski | 606/215 |
| 2005/0283105 A1 | 12/2005 | Heaton et al. | 128/897 |
| 2006/0015087 A1 | 1/2006 | Risk et al. | 604/541 |
| 2006/0029650 A1 | 2/2006 | Coffey | 424/443 |
| 2006/0029675 A1 | 2/2006 | Ginther | 424/486 |
| 2006/0041247 A1 | 2/2006 | Petrosenko et al. | 604/543 |
| 2006/0079852 A1 | 4/2006 | Bubb | 604/317 |
| 2006/0129137 A1 | 6/2006 | Lockwood et al. | 604/543 |
| 2006/0149170 A1 | 7/2006 | Boynton et al. | 601/6 |
| 2006/0149171 A1 | 7/2006 | Vogel et al. | 601/11 |
| 2006/0173253 A1 | 8/2006 | Ganapathy et al. | 600/310 |
| 2006/0189910 A1 | 8/2006 | Johnson et al. | 602/42 |
| 2006/0213527 A1 | 9/2006 | Argenta et al. | 128/898 |
| 2007/0014837 A1 | 1/2007 | Johnson et al. | 424/443 |
| 2007/0021697 A1 | 1/2007 | Ginther et al. | 602/1 |
| 2007/0021698 A1 | 1/2007 | Fleischmann | 602/2 |
| 2007/0005028 A1 | 2/2007 | Risk et al. | 604/315 |
| 2007/0032778 A1 | 2/2007 | Heaton et al. | 604/540 |
| 2007/0038172 A1 | 2/2007 | Zamierowski | 604/20 |
| 2007/0156104 A1 | 7/2007 | Lockwood et al. | 604/305 |
| 2007/0233022 A1 | 10/2007 | Henley et al. | 604/304 |
| 2009/0082740 A1 | 3/2009 | Lockwood et al. | 602/41 |
| 2010/0063483 A1 | 3/2010 | Adahan | 604/543 |

FOREIGN PATENT DOCUMENTS

| | | |
|---|---|---|
| AU | 755496 | 2/2002 |
| CA | 1127488 | 7/1982 |
| CA | 2005436 | 6/1990 |
| CA | 2303085 | 3/1999 |
| CA | 2596321 | 2/2000 |
| DE | 0372727 | 3/1923 |
| DE | 2640413 | 3/1978 |
| DE | 2809828 | 9/1978 |
| DE | 3102674 | 9/1982 |
| DE | 3539533 | 5/1987 |
| DE | 4012232 | 10/1991 |
| DE | 4111122 | 4/1993 |
| DE | 4306478 | 9/1994 |
| DE | 29504378 | 10/1995 |
| DE | 29715634 | 11/1997 |
| DE | 19722075 | 10/1998 |
| DK | 0064055 | 10/1945 |
| EP | 0 100 148 | 2/1984 |
| EP | 0 117 632 | 9/1984 |
| EP | 0 161 865 | 11/1985 |
| EP | 0 358 302 | 3/1990 |
| EP | 0 424 165 | 4/1991 |
| EP | 0 485 657 | 5/1992 |

(56) References Cited

FOREIGN PATENT DOCUMENTS

| | | |
|---|---|---|
| EP | 0 547 496 | 6/1993 |
| EP | 0 730 845 | 9/1996 |
| EP | 0 853 950 | 7/1998 |
| EP | 0 777 504 | 10/1998 |
| EP | 0 880 953 | 12/1998 |
| EP | 1 088 569 | 4/2001 |
| EP | 1 100 574 | 5/2001 |
| EP | 1 190 732 | 3/2002 |
| EP | 1 018 967 | 8/2004 |
| EP | 1 726 276 | 11/2006 |
| FR | 500253 | 3/1920 |
| FR | 1303238 | 7/1962 |
| GB | 3090 | 6/1902 |
| GB | 641061 | 8/1950 |
| GB | 692578 | 6/1953 |
| GB | 1549756 | 8/1979 |
| GB | 1584772 | 2/1981 |
| GB | 2195255 | 4/1988 |
| GB | 2197789 | 6/1988 |
| GB | 2220357 | 1/1990 |
| GB | 2235877 | 3/1991 |
| GB | 2307180 | 5/1997 |
| GB | 2329127 | 3/1999 |
| GB | 2333965 | 8/1999 |
| GB | 2336546 | 10/1999 |
| GB | 2342584 | 4/2000 |
| GB | 2344531 | 6/2000 |
| GB | 2351025 | 12/2000 |
| GB | 2356148 | 5/2001 |
| HU | 199304 | 1/1989 |
| HU | 51150 | 4/1990 |
| HU | 205557 | 4/1990 |
| HU | P9006526 | 1/1993 |
| HU | P9302966 | 7/1996 |
| HU | 76351 | 8/1997 |
| HU | 215563 | 8/1997 |
| HU | 1666 | 12/1999 |
| JP | 57-177758 | 11/1982 |
| JP | 4-129536 | 4/1992 |
| JP | H6-14995 | 1/1994 |
| JP | 6-327761 | 11/1994 |
| JP | H10-504484 | 5/1998 |
| JP | 2001-283352 | 10/2001 |
| JP | 2001-524850 | 12/2001 |
| SE | 0084485 | 10/1935 |
| SG | 71559 | 4/2002 |
| SU | 587941 | 1/1978 |
| SU | 1268175 | 11/1986 |
| WO | WO 1980/002182 | 10/1980 |
| WO | WO 1987/004626 | 8/1987 |
| WO | WO 1989/004158 | 5/1989 |
| WO | WO 1990/010424 | 9/1990 |
| WO | WO 1990/011795 | 10/1990 |
| WO | WO 1991/000718 | 1/1991 |
| WO | WO 1991/008793 | 6/1991 |
| WO | WO 1991/016030 | 10/1991 |
| WO | WO 1992/012750 | 8/1992 |
| WO | WO 1992/019313 | 11/1992 |
| WO | WO 1992/020299 | 11/1992 |
| WO | WO 1993/009715 | 3/1993 |
| WO | WO 1993/009727 | 5/1993 |
| WO | WO 1994/000090 | 1/1994 |
| WO | WO 1994/20041 | 9/1994 |
| WO | WO 1996/005873 | 2/1996 |
| WO | WO 1996/015745 | 5/1996 |
| WO | WO 1997/018007 | 3/1997 |
| WO | WO 1998/002205 | 1/1998 |
| WO | WO 1998/038944 | 9/1998 |
| WO | WO 1999/001173 | 1/1999 |
| WO | WO 1999/013793 | 3/1999 |
| WO | WO 1999/023990 | 5/1999 |
| WO | WO 1999/059816 | 11/1999 |
| WO | WO 2000/007653 | 2/2000 |
| WO | WO 2000/015277 | 3/2000 |
| WO | WO 2000/021586 | 4/2000 |
| WO | WO 2000/026100 | 5/2000 |
| WO | WO 2000/028890 | 5/2000 |
| WO | WO 2000/030567 | 6/2000 |
| WO | WO 2000/032247 | 6/2000 |
| WO | WO 2000/038552 | 7/2000 |
| WO | WO 2000/038755 | 7/2000 |
| WO | WO 2000/042958 | 7/2000 |
| WO | WO 2000/059418 | 10/2000 |
| WO | WO 2000/059424 | 10/2000 |
| WO | WO 2000/061206 | 10/2000 |
| WO | WO 2000/064394 | 11/2000 |
| WO | WO 2001/034223 | 5/2001 |
| WO | WO 2001/037922 | 5/2001 |
| WO | WO 2001/049233 | 7/2001 |
| WO | WO 2001/085248 | 11/2001 |
| WO | WO 2001/089431 | 11/2001 |
| WO | WO 2002/038091 | 5/2002 |
| WO | WO 2002/043634 | 6/2002 |
| WO | WO 2003/005943 | 1/2003 |
| WO | WO 2003/045492 | 6/2003 |
| WO | WO 2003/057071 | 7/2003 |
| WO | WO 2003/057307 | 7/2003 |
| WO | WO 2003/101508 | 12/2003 |

OTHER PUBLICATIONS

Notice of Allowance issued in U.S. Appl. No. 10/509,137, dated Dec. 7, 2011. US).
Office Communication issued in Canadian Patent Application No. 2,689,308, dated Dec. 19, 2011.
Office Communication issued in European Patent Application No. 01 998 292.5, dated Feb. 16, 2002.
Office Communication issued in U.S. Appl. No. 12/328,531, dated Jan. 6, 2012.
Office Communication issued in U.S. Appl. No. 12/328,531, dated Mar. 16, 2012.
Office Communication issued in U.S. Appl. No. 12/860,581, dated Nov. 3, 2011.
Office Communication issued in U.S. Appl. No. 12/860,581, dated Jan. 18, 2012.
Office Communication issued in U.S. Appl. No. 12/860,581, dated Feb. 24, 2012.
U.S. Appl. No. 12/618,411, filed Nov. 13, 2009.
U.S. Appl. No. 12/860,851, filed Aug. 20, 2011.
U.S. Appl. No. 12/328,531, filed Dec. 4, 2008.
U.S. Appl. No. 11/242,543, filed Oct. 3, 2005.
U.S. Appl. No. 10/509,137, filed Sep. 27, 2004.
"Jump-Start Wound Healing with OASIS," *Wounds*, Special Supplement, 13(2):1-28, 2001.
"Oasis™ Wound Dressing," *SIS™ Technology*, pp. 1-4, Sep. 2001.
"Surgisis™ Soft-Tissue Graft," *SIS™ Technology*, pp. 1-4, Sep. 2001.
Abdullah, "A new method for fixation of drainage catheters," *Journal of Hong Kong College of Radiologists*, 4:272-273, 2001.
Advisory Action issued in U.S. Appl. No. 10/509,137, dated Jun. 24, 2010.
Advisory Action issued in U.S. Appl. No. 10/885,431, dated Dec. 8, 2009.
Advisory Action issued in U.S. Appl. No. 11/051,283, dated May 5, 2010.
Advisory Action issued in U.S. Appl. No. 11/515,983, dated Feb. 1, 2010.
Advisory Action issued in U.S. Appl. No. 11/761,066, dated Feb. 16, 2010.
Argenta et al., "Vacuum-assisted closure: a new method for wound control and treatment: Clinical experience," *Annals of Plastic Surgery*, 38(6):563-577, 1997.
Argenta et al., Patent Application entitled "The enhancement of wound healing and flap survival by a new negative pressure device," 30 pages, 1997.
Arnljots and Svedman, "Irrigation Treatment in Split-Thickness Skin Grafting of Intractable Leg Ulcers," *Scand J. Plast Reconstr. Surg.*, 19(2):211-213, 1985.

(56) References Cited

OTHER PUBLICATIONS

Bagautdinov, "Variant of external vacuum aspiration in the treatment of purulent diseases of soft tissues," *Current Problems in Modern Clinical Surgery: Interdepartmental Collection*, edited by V. Ye Volkov et al. (Chuvashia State University, Cheboksary, U.S.S.R. 1986);pp. 9496 (certified translation).
Blackburn II et al.; "Negative-pressure dressings as a bolster for skin grafts," *Annals of Plastic Surgery*, 40(5):453-457, 1998.
Borzov et al., "Vacuum therapy of some skin diseases," *Vestn. Dermatol. Venerol.* (English translation), Aug. 1965.
Brochure—"Cavi-Care," *Smith & Nephew*, 2000.
Brochure—Aeros—Care-E-Vac; 2 pages, 1988.
Brochure—Aeros—Instavac Aspirator; 1 page, 1988.
Brochure—Aeros—Moblvacll, 1 page, 1988.
Brochure—Augustine Medical, Warm-Up Active Wound Therapy Wound Covers, 3 pages, 1999.
Brochure—Emerson Transport Suction Unit; 1 page, 1995.
Brochure—Healthpoint® Oasis® Wound Matrix, *Cook Biotech Incorporated*, 2003.
Brochure—Hiblow Air Pump; 1 page, 1999.
Brochure—KCI—The V.A.C. (Vacuum Assisted Closure), 7 pages, 1998.
Brochure—Microtek Heritage, Inc.—The Wound-Evac ET, Closed Wound Suction System, 4 pages, 1986.
Brochure—Pleur-evac Adult-Pediatric-Non-Metered Disposable "3-bottle" Unit, A-4000; 6 pages, 1995.
Brochure—Series 55—Emerson Post-Operative Suction Pumps; 1 page, 1996.
Brochure—Wells Johnson Company—Point 5 Aspirator; 2 pages, 1988.
Brochure/Instruction Manual—Creative Medical Laboratories, Inc.—TUGS (Transportable Universal Gradient Suction) System, 1984.
Bucalo et al., "Inhibition of cell proliferation by chronic wound fluid," *Wound Repair and Regeneration*, 181-186, 1993.
Chariker et al., "Effective management of incisional and cutaneous fistulae with closed suction wound drainage," *Contemporary Surgery*, 34:59-63, 1989.
Chinn and Burns, "Closed wound suction drainage," *The Journal of Foot Surgery*, 24(1):76-81, 1985.
Comment-Ruckley et al., "Vacuum drainage of groin wounds after vascular surgery," pp. 505-506, 1991.
Communication of Notice of Opposition issued in European Application No. 07001838.7, dated Apr. 28, 2010 (and Opposition).
Communication of Notice of Opposition issued in European Pat. No. 1772160, dated Mar. 26, 2010.
Dattilo, Jr. et al.; "Medical textiles: application of an absorbable barbed bi-directional surgical suture"; *Journal of Textile and Apparel, Technology and Management*, 2(2):1-5, 2002.
Davydov et al., "Bacteriological and cytological assessment of vacuum therapy for purulent wounds," *Vestnik Khirurgi*, pp. 48-52 (and 8 page English translation thereof), Oct. 1988.
Davydov et al., "Basis of the use of forced early secondary suture in the treatment of suppurative wounds by the vacuum therapy method," *Vestn. Khir.* (English translation), Mar. 1990.
Davydov et al., "Concepts for the clinical-biological management of the wound process in the treatment of purulent wounds by means of vacuum therapy," *Vestnik Khirurgi*, pp. 132-136 (and 8 page English translation thereof), Jul. 1980.
Davydov et al., "Pathogenic mechanism of the effect of vacuum therapy on the course of the wound process," *Khirurgiia*, (English translation), Jun. 1990.
Davydov et al., "Vaccuum therapy in the treatment of acute suppurative diseases of soft tissues and suppurative wounds," *Vestn. Khir.* (English translation), Sep. 1988.
Davydov et al., "Vacuum Therapy in the Treatment of Purulent Lactation Mastitis," *Vestnik Khirurgi*, pp. 66-70 (and 9 page English translation thereof), May 1986.
Decision on Appeal issued in U.S. Appl. No. 10/276,778, dated Mar. 6, 2010.

Decision on Appeal issued in U.S. Appl. No. 11/242,543, dated Mar. 5, 2010.
Definition of "pore," provided by Merriam-Webster Online Dictionary, printed Apr. 5, 2010.
Definition of "porous," provided by Merriam-Webster Online Dictionary, printed Apr. 5, 2010.
Dunlop et al., "Vacuum drainage of groin wounds after vascular surgery: A controlled trial," *Br. J. Surg.*, 77:562-563, 1990.
Egnell Minor, Instruction Book, First Edition, 300, 7502, pp. 24, Feb. 1975.
Egnell Minor: Addition to the Users Manual Concerning Overflow Protection—Concerns all Egnell Pumps, Feb. 3, 1983, pp. 2.
Fleischmann, "Vacuum sealing for treatment of problematic wounds," *WundForum Spezial IHW* (English translation), pp. 54-55, 1994.
Fleishmann et al., "Vacuum sealing for treatment of soft tissue injury in open fractures," *Unfallchirurg*, 96:488-492, 1993. (English translation of summary provided).
Fourth SIS-ECM Symposium, Phoenix, Arizona, Dec. 6-7, 2002.
Genecov et al., "A controlled subatmospheric pressure dressing increases the reate of skin graft donor site reepithelialization," *Annals of Plastic Surgery*, 40(3):219-225, 1998.
Greer et al., "The use of subatmospheric pressure dressing therapy to close lymphocutaneous fistulas of the groin," *British Journal of Plastic Surgery*, 53(6):484-487, 2000.
Jeter et al., "Managing draining wounds and fistulae: new and established methods," *Chronic Wound Care*, 27:240-246, 1990.
Johnson, "An improved technique for skin graft placement using a suction drain," *Surgery, Gynecology, and Obstetrics*, 159(6):584-585, 1984.
Kinetic Concepts, Inc., Form 10-K—Annual report pursuant to section 13 or 15(d) of the Securities Exchange Act of 1934, for the fiscal year ended Dec. 31, 2006, United States Securities and Exchange Commission, pp. 1, 2, 3, 12, 13, and 14.
Klein, "Cook Incorporated forms dedicated tissue engineered products group," *PR Newswire*, 2000.
Kostyuchenok et al., "Vacuum treatment in the surgical management of purulent wounds"; *Vestnik Khirurgi*, pp. 18-21 (and 6 page English translation thereof), Sep. 1986.
Kuznetsov and Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92, Oct. 1986.
Landis et al., "The effects of alternative suction and pressure on blood flow to the lower extremities," *Alternate Suction and Pressure*, pp. 925-961.
Letsou et al., "Stimulation of adenylate cyclase activity in cultured endothelial cells subjected to cyclic stretch," *Journal of Cardiovascular Surgery*, 31:634-639, 1990.
Letter and Memo reporting Office Action issued in Mexican Application No. PA/a/2001/001124, dated Jul. 13, 2004.
Lundvall et al., "Transmission of externally applied negative pressure to the underlying tissue. A study on the upper arm of man," *Acta Physiol. Scand.*, 136:403-409, 1989.
Masters, "Reliable, inexpensive and simple suction dressings," Letter to the Editor, *British Journal of Plastic Surgery*, Elsevier Science/The British Association of Plastic Surgeons, UK, 51(3):267, 1998.
McCarty, "Cook Incorporated forms dedicated tissue engineered products group," *Cook® Online, News and Media Information*, 2000.
Medical Industry Week, "KCI offers new treatment for non-healing wounds," 1 page, 1989.
Mendez-Eastman, "When wounds won't heal," *RN*, 61(1):20-24, 1998.
Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.
Mirazimov et al., "Free skin graft of the foot with preparation of the wound surface by vacuum treatment," *Ortop. Travmatol Protez.* (English translation), Oct. 1966.

(56) References Cited

OTHER PUBLICATIONS

Morykwas et al., "Nonsurgical modalities to enhance healing and care of soft tissue wounds," www.sma.org/soa/jsoawt97, Feb. 11, 1999.
Morykwas et al., "Use of negative pressure to increase the rate of granulation tissue formation in chronic open wounds," *Extracellular Matrix and Healing*, p. 800, 1993.
Morykwas et al., "Vacuum-assisted closure: a new method for wound control and treatment: Animal studies and basic foundation," *Annals of Plastic Surgery*, (6):553-562, 1997.
Mulder et al., "Clinicians' pocket guide to chronic wound repair," *Wound Healing Publications*, 1991.
Nakayama et al., "A new dressing method for free skin grafting in hands," *Ann. Plast. Surg.*, 26(5):499-502, 1991.
Nakayama et al., "A new method for the dressing of free skin grafts," *Plast. Reconstr. Surg.*, 86(6):1216-1219, 1990.
Neumann et al., "Gelatin-based sprayable foam as a skin substitute," *J. of Biomed Materials Research*, 15:9-18, 1981.
Notice of Allowance issued in U.S. Appl. No. 10/276,778, dated May 21, 2010.
Notice of Allowance issued in U.S. Appl. No. 10/276,778, dated Sep. 7, 2010.
Notice of Allowance issued in U.S. Appl. No. 10/524,957, dated Oct. 14, 2010.
Notice of Allowance issued in U.S. Appl. No. 10/664,535, dated Jun. 2, 2010.
Notice of Allowance issued in U.S. Appl. No. 10/664,535, dated Sep. 9, 2010.
Notice of Allowance issued in U.S. Appl. No. 10/885,431, dated Mar. 22, 2010.
Notice of Allowance issued in U.S. Appl. No. 11/051,283, dated Mar. 29, 2011.
Notice of Allowance issued in U.S. Appl. No. 11/230,988, dated Dec. 3, 2010.
Notice of Allowance issued in U.S. Appl. No. 11/242,543, dated Sep. 27, 2010.
Notice of Allowance issued in U.S. Appl. No. 11/515,983, dated May 17, 2011.
Notice of Allowance issued in U.S. Appl. No. 11/684,989, dated Nov. 8, 2010.
Notice of Allowance issued in U.S. Appl. No. 11/761,066, dated May 13, 2010.
Office Action issued in Australian Application No. 5255/99, dated Aug. 6, 2002.
Office Action issued in Canadian Application No. 2,338,443, dated Feb. 7, 2006.
Office Action issued in Canadian Application No. 2,390,131, dated Jul. 20, 2007.
Office Action issued in Canadian Application No. 2,467,837, dated May 27, 2009.
Office Action issued in Canadian Application No. 2,481,016, dated Aug. 13, 2009.
Office Action issued in Canadian Application No. 2,481,016, dated Jun. 15, 2010.
Office Action issued in Canadian Application No. 2,481,016, dated Apr. 1, 2011.
Office Action issued in Czech Republic Application No. PV2001-497, dated Feb. 7, 2001.
Office Action issued in European Application No. 00991498.7, dated Dec. 17, 2003.
Office Action issued in European Application No. 00991498.7, dated Jan. 2, 2006.
Office Action issued in European Application No. 01 998 292.5, dated May 7, 2010.
Office Action issued in European Application No. 01998292.5, dated Feb. 18, 2005.
Office Action issued in European Application No. 01998292.5, dated Jul. 17, 2006.
Office Action issued in European Application No. 01998292.5, dated Sep. 12, 2008.
Office Action issued in European Application No. 02 794 388.5, dated Feb. 10, 2011.
Office Action issued in European Application No. 02 794 392.7, dated May 3, 2011.
Office Action issued in European Application No. 02 794 394.3, dated Nov. 26, 2010.
Office Action issued in European Application No. 02 794 394.3, dated Jun. 14, 2011.
Office Action issued in European Application No. 02 794 397.6, dated Oct. 12, 2010.
Office Action issued in European Application No. 02784588.2, dated Sep. 15, 2005.
Office Action issued in European Application No. 03 734 294.6, dated Apr. 21, 2011.
Office Action issued in European Application No. 08010957.2, dated Apr. 8, 2009.
Office Action issued in European Application No. 99 937 799, dated Aug. 18, 2003.
Office Action issued in Japanese Application No. 2001-539532, dated May 11, 2010 (and English language translation thereof).
Office Action issued in Japanese Application No. 2004-508861, dated Apr. 14, 2009, and English language translation thereof.
Office Action issued in Japanese Application No. 2004-508861, dated Feb. 16, 2010, and English language translation thereof.
Office Action issued in Japanese Application No. 2008-007788, dated Oct. 5, 2010.
Office Action issued in Japanese Application No. 2008-007788, dated Jun. 28, 2011. (English translation).
Office Action issued in Japanese Patent Application No. 2009-236963, dated Aug. 2, 2011. (English translation).
Office Action issued in Polish Application No. P-357 417, dated Nov. 25, 2008; English translation.
Office Action issued in Polish Application No. P-364 754, 2006.
Office Action issued in U.S. Appl. No. 09/369,113, dated Jan. 31, 2001.
Office Action issued in U.S. Appl. No. 09/725,352, dated Dec. 12, 2002.
Office Action issued in U.S. Appl. No. 09/743,737, dated Aug. 11, 2006.
Office Action issued in U.S. Appl. No. 09/743,737, dated Apr. 1, 2003.
Office Action issued in U.S. Appl. No. 09/743,737, dated Jun. 19, 2002.
Office Action issued in U.S. Appl. No. 09/743,737, dated Oct. 23, 2002.
Office Action issued in U.S. Appl. No. 09/743,737, dated Sep. 8, 2005.
Office Action issued in U.S. Appl. No. 09/855,287, dated Dec. 15, 2003.
Office Action issued in U.S. Appl. No. 09/855,287, dated Jul. 14, 2005.
Office Action issued in U.S. Appl. No. 09/855,287, dated Jun. 24, 2004.
Office Action issued in U.S. Appl. No. 09/855,287, dated Oct. 1, 2002.
Office Action issued in U.S. Appl. No. 09/994,537, dated Jan. 16, 2003.
Office Action issued in U.S. Appl. No. 09/994,537, dated Jun. 30, 2003.
Office Action issued in U.S. Appl. No. 10/144,504, dated May 14, 2004.
Office Action issued in U.S. Appl. No. 10/267,358, dated Jun. 29, 2005.
Office Action issued in U.S. Appl. No. 10/276,778, dated Aug. 7, 2008.
Office Action issued in U.S. Appl. No. 10/276,778, dated Apr. 24, 2006.
Office Action issued in U.S. Appl. No. 10/276,778, dated Jul. 13, 2007.
Office Action issued in U.S. Appl. No. 10/276,778, dated Mar. 22, 2007.
Office Action issued in U.S. Appl. No. 10/276,778, dated Nov. 19, 2007.

(56) References Cited

OTHER PUBLICATIONS

Office Action issued in U.S. Appl. No. 10/276,778, dated Oct. 11, 2006.
Office Action issued in U.S. Appl. No. 10/496,360, dated Jun. 2, 2009.
Office Action issued in U.S. Appl. No. 10/496,360, dated Jun. 12, 2006.
Office Action issued in U.S. Appl. No. 10/496,360, dated Mar. 26, 2008.
Office Action issued in U.S. Appl. No. 10/496,360, dated Mar. 14, 2007.
Office Action issued in U.S. Appl. No. 10/496,360, dated Oct. 3, 2008.
Office Action issued in U.S. Appl. No. 10/496,360, dated Oct. 5, 2006.
Office Action issued in U.S. Appl. No. 10/496,360, dated Sep. 10, 2007.
Office Action issued in U.S. Appl. No. 10/496,623, dated Jun. 9, 2006.
Office Action issued in U.S. Appl. No. 10/509,137, dated Apr. 9, 2010.
Office Action issued in U.S. Appl. No. 10/509,137, dated Apr. 28, 2011.
Office Action issued in U.S. Appl. No. 10/509,137, dated Dec. 20, 2007.
Office Action issued in U.S. Appl. No. 10/509,137, dated Dec. 8, 2010.
Office Action issued in U.S. Appl. No. 10/509,137, dated Jun. 3, 2009.
Office Action issued in U.S. Appl. No. 10/509,137, dated Jun. 22, 2007.
Office Action issued in U.S. Appl. No. 10/509,137, dated Jan. 10, 2007.
Office Action issued in U.S. Appl. No. 10/509,137, dated Nov. 24, 2008.
Office Action issued in U.S. Appl. No. 10/524,957, dated Apr. 11, 2007.
Office Action issued in U.S. Appl. No. 10/524,957, dated Aug. 10, 2007.
Office Action issued in U.S. Appl. No. 10/524,957, dated Apr. 15, 2008.
Office Action issued in U.S. Appl. No. 10/524,957, dated Aug. 3, 2009.
Office Action issued in U.S. Appl. No. 10/524,957, dated Feb. 25, 2010.
Office Action issued in U.S. Appl. No. 10/524,957, dated Jul. 26, 2010.
Office Action issued in U.S. Appl. No. 10/524,957, dated Sep. 30, 2008.
Office Action issued in U.S. Appl. No. 10/664,535, dated Apr. 17, 2008.
Office Action issued in U.S. Appl. No. 10/664,535, dated Apr. 2, 2007.
Office Action issued in U.S. Appl. No. 10/664,535, dated Dec. 15, 2009.
Office Action issued in U.S. Appl. No. 10/664,535, dated Mar. 1, 2006.
Office Action issued in U.S. Appl. No. 10/664,535, dated Oct. 26, 2007.
Office Action issued in U.S. Appl. No. 10/664,535, dated Oct. 16, 2006.
Office Action issued in U.S. Appl. No. 10/885,431, dated Apr. 15, 2008.
Office Action issued in U.S. Appl. No. 10/885,431, dated Jun. 24, 2009.
Office Action issued in U.S. Appl. No. 10/885,431, dated Mar. 22, 2007.
Office Action issued in U.S. Appl. No. 10/885,431, dated Sep. 26, 2008.
Office Action issued in U.S. Appl. No. 10/885,431, dated Sep. 19, 2007.
Office Action issued in U.S. Appl. No. 10/885,431, dated Sep. 11, 2006.
Office Action issued in U.S. Appl. No. 10/997,612, dated Apr. 30, 2007.
Office Action issued in U.S. Appl. No. 10/997,612, dated Mar. 20, 2008.
Office Action issued in U.S. Appl. No. 10/997,612, dated May 5, 2006.
Office Action issued in U.S. Appl. No. 10/997,612, dated Nov. 14, 2008.
Office Action issued in U.S. Appl. No. 10/997,612, dated Nov. 19, 2007.
Office Action issued in U.S. Appl. No. 10/997,612, dated Oct. 31, 2006.
Office Action issued in U.S. Appl. No. 11/051,283, dated Feb. 22, 2006.
Office Action issued in U.S. Appl. No. 11/051,283, dated Feb. 25, 2010.
Office Action issued in U.S. Appl. No. 11/051,283, dated Jun. 5, 2009.
Office Action issued in U.S. Appl. No. 11/051,283, dated Jan. 9, 2008.
Office Action issued in U.S. Appl. No. 11/051,283, dated Mar. 22, 2007.
Office Action issued in U.S. Appl. No. 11/051,283, dated Oct. 17, 2008.
Office Action issued in U.S. Appl. No. 11/051,283, dated Oct. 15, 2010.
Office Action issued in U.S. Appl. No. 11/051,283, dated Sep. 7, 2007.
Office Action issued in U.S. Appl. No. 11/051,283, dated Sep. 29, 2006.
Office Action issued in U.S. Appl. No. 11/051,283, dated Sep. 7, 2005.
Office Action issued in U.S. Appl. No. 11/230,988, dated Apr. 16, 2009.
Office Action issued in U.S. Appl. No. 11/230,988, dated Aug. 26, 2009.
Office Action issued in U.S. Appl. No. 11/230,988, dated Mar. 26, 2008.
Office Action issued in U.S. Appl. No. 11/230,988, dated Mar. 13, 2007.
Office Action issued in U.S. Appl. No. 11/230,988, dated May 26, 2010.
Office Action issued in U.S. Appl. No. 11/230,988, dated Oct. 3, 2008.
Office Action issued in U.S. Appl. No. 11/230,988, dated Oct. 15, 2010.
Office Action issued in U.S. Appl. No. 11/230,988, dated Sep. 28, 2006.
Office Action issued in U.S. Appl. No. 11/230,988, dated Sep. 10, 2007.
Office Action issued in U.S. Appl. No. 11/242,543, dated May 18, 2007.
Office Action issued in U.S. Appl. No. 11/242,543, dated Oct. 20, 2006.
Office Action issued in U.S. Appl. No. 11/242,543, dated Oct. 25, 2007.
Office Action issued in U.S. Appl. No. 11/347,073, dated Apr. 1, 2008.
Office Action issued in U.S. Appl. No. 11/515,983, dated May 11, 2009.
Office Action issued in U.S. Appl. No. 11/515,983, dated May 7, 2010.
Office Action issued in U.S. Appl. No. 11/515,983, dated Nov. 20, 2009.
Office Action issued in U.S. Appl. No. 11/515,983, dated Oct. 5, 2010.
Office Action issued in U.S. Appl. No. 11/684,989, dated Dec. 29, 2009.

(56) References Cited

OTHER PUBLICATIONS

Office Action issued in U.S. Appl. No. 11/684,989, dated Jul. 7, 2009.
Office Action issued in U.S. Appl. No. 11/684,989, dated Jun. 29, 2010.
Office Action issued in U.S. Appl. No. 11/684,989, dated Nov. 18, 2008.
Office Action issued in U.S. Appl. No. 11/761,066, dated Dec. 13, 2007.
Office Action issued in U.S. Appl. No. 11/761,066, dated Dec. 9, 2009.
Office Action issued in U.S. Appl. No. 11/761,066, dated Jun. 2, 2009.
Office Action issued in U.S. Appl. No. 11/761,066, dated Oct. 28, 2008.
Office Action issued in U.S. Appl. No. 11/761,066, dated Sep. 25, 2007.
Office Action issued in U.S. Appl. No. 12/328,531, dated Jun. 13, 2011.
Olenius et al., "Mitotic activity in expanded human skin," *Plastic and Reconstructive Surgery*, pp. 213-215, 1993.
Oosterbroek et al., "A micromachined pressure/flow-sensor," *Sensor and Actuators*, 77(3):167177, 1999. Abstract Only.
Orringer et al., "Management of wounds in patients with complex enterocutaneous fistulas," *Surgery, Gynecology & Obstetrics*, 165:79-80, 1987.
Patent Application entitled "Method of treating tissue damage and apparatus for same," 28 pages. (U.S. Pat. No. 5,645,081 included as A reference).
PCT Declaration of Non-Establishment of International Search Report issued in International Application No. PCT/US2003/17099, dated Nov. 7, 2003.
PCT International Preliminary Examination Report issued in International Application No. PCT/GB1996/02802, dated Jan. 15, 1998.
PCT International Preliminary Examination Report issued in International Application No. PCT/US1999/17877, dated Oct. 30, 2001.
PCT International Preliminary Examination Report issued in International Application No. PCT/US2000/42333, dated Nov. 19, 2002.
PCT International Preliminary Examination Report issued in International Application No. PCT/US2001/44194, dated Dec. 3, 2003.
PCT International Search Report issued in International Application No. PCT/GB1998/02713, dated Jan. 8, 1999.
PCT International Search Report issued in International Application No. PCT/GB1995/01983, dated Nov. 23, 1995.
PCT International Search Report issued in International Application No. PCT/GB1996/02802, dated Apr. 29, 1997.
PCT International Search Report issued in International Application No. PCT/US2002/32221, dated Feb. 5, 2003.
PCT International Search Report issued in International Application No. PCT/US2000/42333, dated Aug. 3, 2001.
PCT International Search Report issued in International Application No. PCT/US2002/41210, dated Oct. 28, 2003.
PCT International Search Report issued in International Application No. PCT/US1999/17877, dated Oct. 27, 1999.
PCT International Search Report issued in International Application No. PCT/US2001/15611, dated Sep. 5, 2001.
PCT International Search Report issued in International Application No. PCT/US2002/41229, dated Jun. 30, 2003.
PCT International Search Report issued in International Application No. PCT/US2002/41300, dated Jul. 31, 2003.
PCT International Search Report issued in International Application No. PCT/US2001/44194, dated Dec. 9, 2002.
PCT International Search Report issued in International Application No. PCT/US2002/41228, dated Jun. 30, 2003.
PCT International Search Report issued in International Application No. PCT/US2002/37814, dated Apr. 7, 2003.
PCT International Search Report issued in International Application No. PCT/US2002/41231, dated May 9, 2003.
PCT International Search Report issued in International Application No. PCT/US2002/41234, dated Oct. 24, 2003.
PCT Written Opinion issued in International Application No. PCT/GB1996/02802, dated Sep. 3, 1997.
PCT Written Opinion issued in International Application No. PCT/GB1998/02713, dated Jun. 8, 1999.
PCT Written Opinion issued in International Application No. PCT/US1999/17877, dated Aug. 20, 2001.
PCT Written Opinion issued in International Application No. PCT/US2000/42333, dated Jun. 24, 2002.
Response to Opposition submitted in European Patent No. EP 1 772 160, filed Sep. 29, 2010.
Roget's New Millenium Thesaurus, First Edition (v 1.3.1), 2007.
Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
Sames, "Sealing of wounds with vacuum drainage," *Br. Med. J.*, 2(6096):1123, 1977.
Schein et al., "The 'Sandwich Technique' in the management of the open abdomen," *British Journal of Surgery*, 73:369-370, 1986.
Schneider et al., "A new and reliable method of securing skin grafts to the difficult recipient bed," *Plastic and Reconstructive Surgery*, pp. 1195-1198, 1998.
Search Report issued in Hungarian Application No. P0103545, dated Oct. 29, 2001.
Search Report issued in Hungarian Application No. P0500055, dated May 3, 2005.
Solovev et al., "Guidelines, the method of treatment of immature external fistulas in the upper gastrointestinal tract," editor-in-chief Prov. V.I. Parahonyak, S.M. Kirov Gorky State Medical Institute, Gorky, U.S.S.R., 1987.
Solovev, Dissertation Abstract, "Treatment and prevention of suture failures after gastric resection," S.M. Kirov Gorky State Medical Institute, Gorky, U.S.S.R., 1988.
Supplemental Notice of Allowability issued in U.S. Appl. No. 10/885,431, dated Apr. 22, 2010.
Supplementary Search Report issued in European Application No. 02794393.5, dated Aug. 1, 2006.
Supplementary Search Report issued in European Application No. 02796039.2, dated Sep. 4, 2009.
Supplementary Search Report issued in European Application No. 02794388.5, dated Jun. 16, 2009.
Supplementary Search Report issued in European Application No. 02794392.7, dated Jun. 5, 2009.
Supplementary Search Report issued in European Application No. 02794394.3, dated Apr. 6, 2009.
Supplementary Search Report issued in European Application No. 02794397.6, dated Jan. 29, 2009.
Supplementary Search Report issued in European Application No. 07001838.7, dated Mar. 5, 2007.
Supplementary Search Report issued in European Application No. 08010957.2, dated Aug. 27, 2008.
Svedman et al., "A dressing system providing fluid supply and suction drainage used for continuous or intermittent irrigation," *Annals of Plastic Surgery*, 17(2):125-133, 1986.
Svedman, "A dressing allowing continuous treatment of a biosurface," *IRCS Medical Science: Biomedical Technology, Clinical Medicine, Surgery and Transplantation*, 7:221, 1979.
Svedman, "Irrigation treatment of leg ulcers," *The Lancet*, 2(8349):532-534, 1983.
Teder et al., "Continuous wound irrigation in the pig," *J. Invest. Surg.*, 3:399-407, 1990.
Tennant, "The use of hypermia in the postoperative treatment of lesions of the extremities and thorax," *Journal of the American Medical Association*, 64:1548-1549, 1915.
Tittel et al., "New standards in postoperative wound drainage," *Eingag und Annahme des Manuskripts*, pp. 104-107, 1987.
Tribble, "An improved sump drain-irrigation device of simple construction," *Archives of Surgery*, 105(3):511-513, 1972.
Valenta, "Using the vacuum dressing alternative for difficult wounds," AIN, pp. 44-45, 1994.
Viljanto et al., "Local hyperalimentation of open wounds," *Br. I Surg.*, 63:427-430, 1976.

(56) References Cited

OTHER PUBLICATIONS

Wolthuis et al., "Physiological effects of locally applied reduced pressure in man," *Physiological Reviews*, 54(3):566-595, 1974.
Wood et al., "Foam elastomer dressing in the management of open granulating wounds: experience with 250 patients," *Br. J. of Surg.*, 64:554-557, 1977.
Wooding-Scott et al., "No wound is too big for resourceful nurses," *RN*, pp. 22-25, 1988.
Yusupov et al., "Active wound drainage," *Vestnik Khirurgi*, 138(4) (and 7 page English translation thereof), 1987.
Živadinović et al., "Vacuum therapy in the treatment of peripheral blood vessels," *Timok Medical Journal*, 11:161-164 (and certified translation), 1986.

* cited by examiner

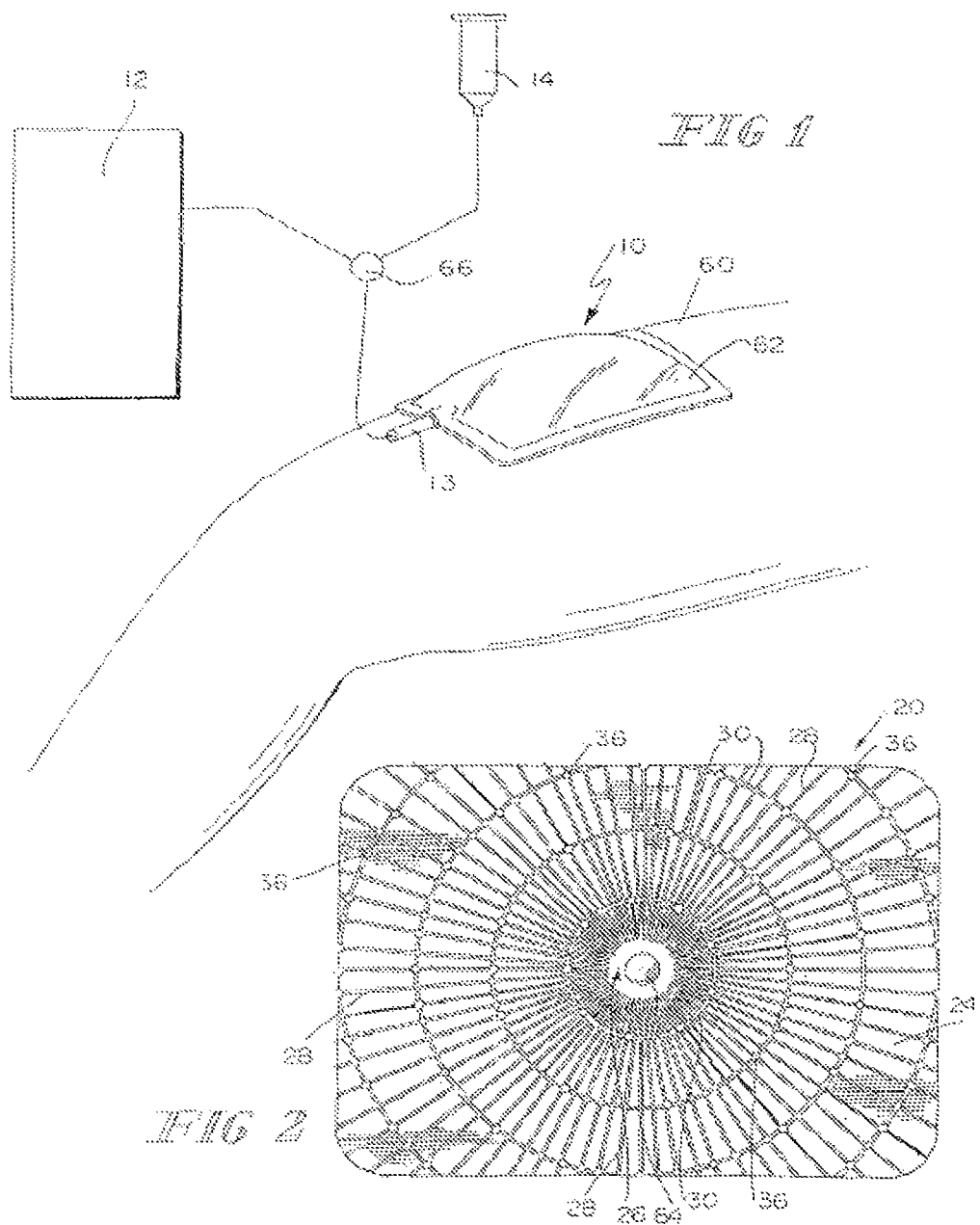

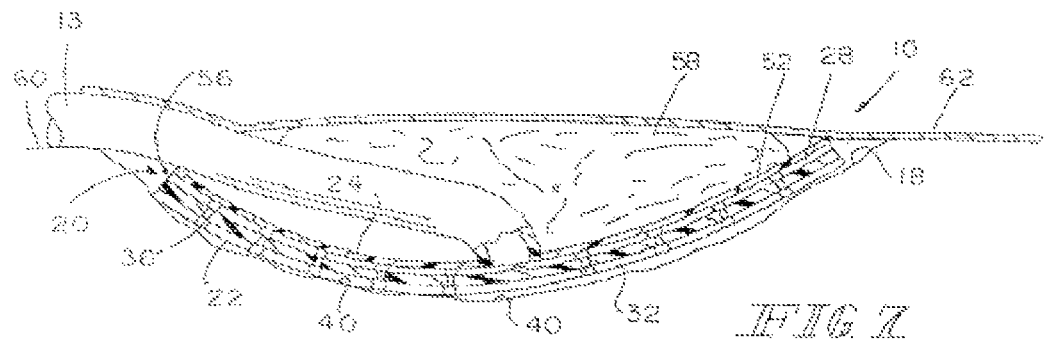
FIG. 7
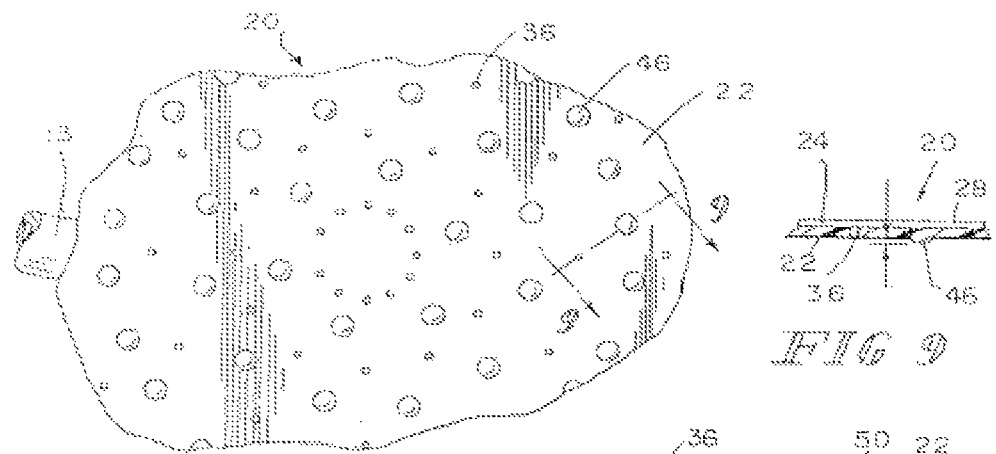
FIG. 8
FIG. 9
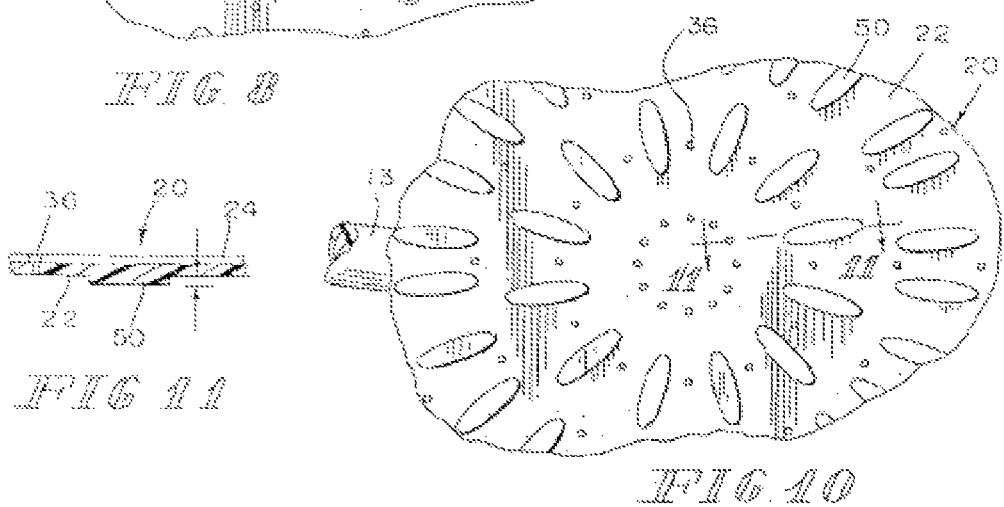
FIG. 11
FIG. 10

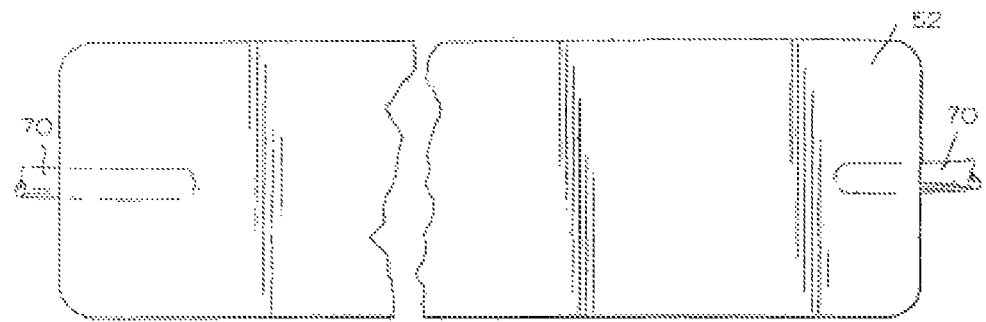
FIG 12
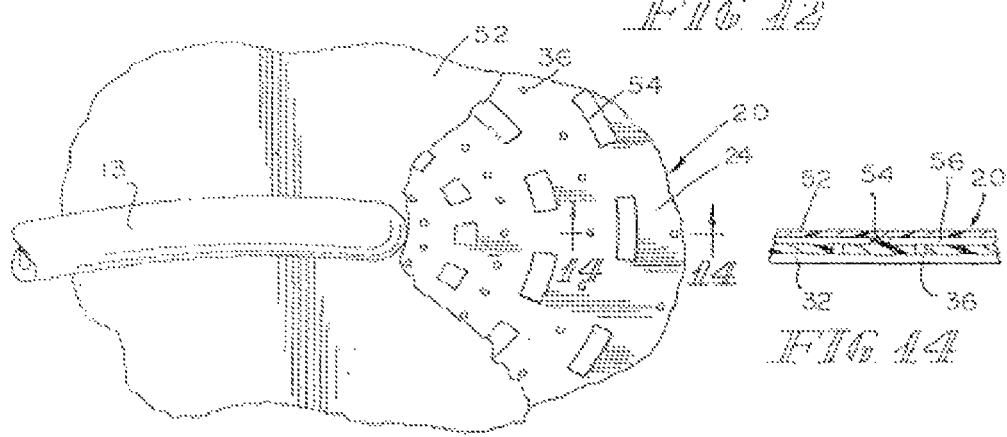
FIG 13
FIG 14
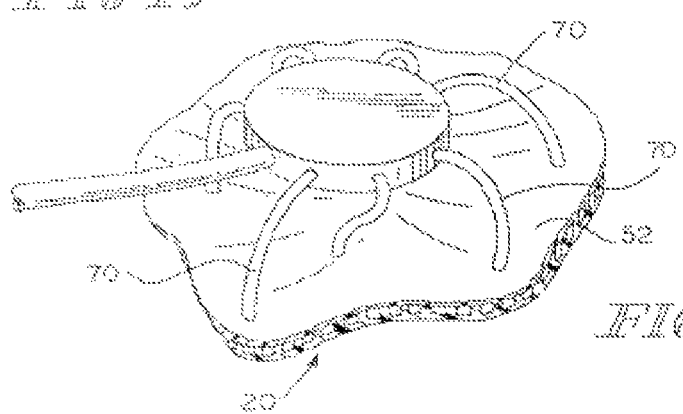
FIG 15

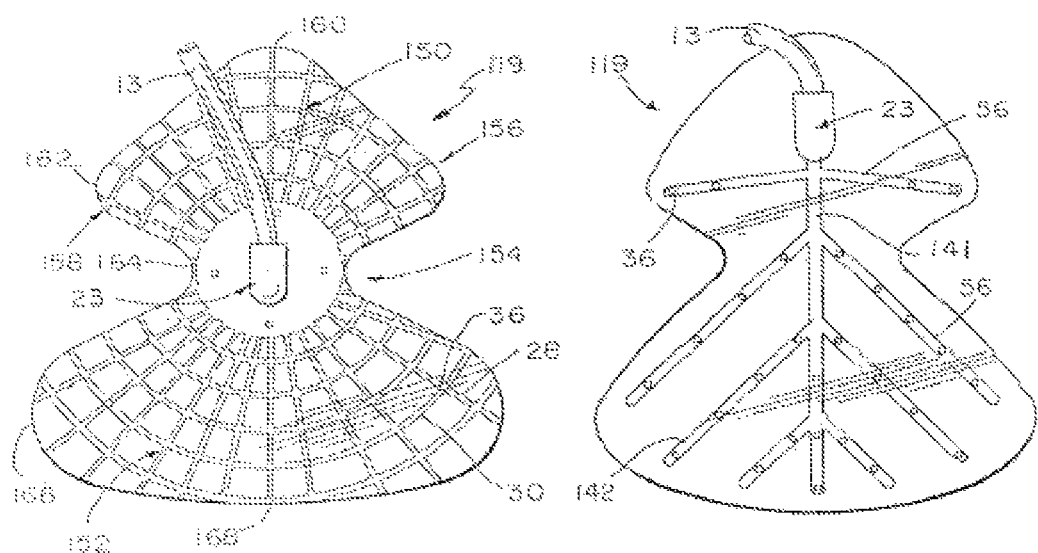
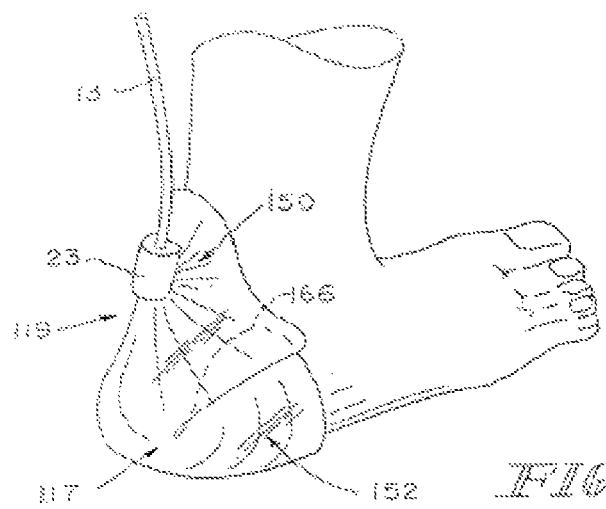

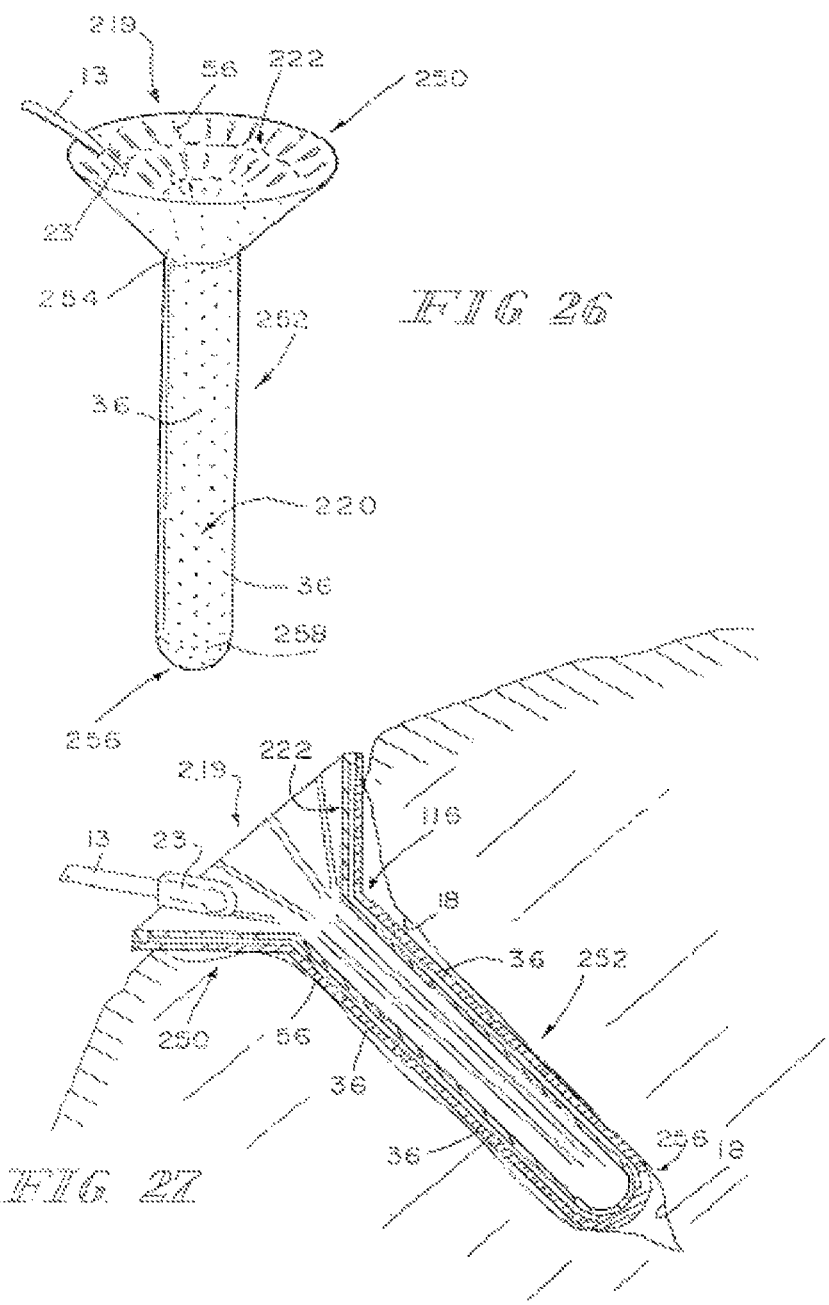

VACUUM THERAPY AND CLEANSING DRESSING FOR WOUNDS

CROSS-REFERENCE TO RELATED APPLICATIONS

This application is a continuation of co-pending U.S. patent application Ser. No. 11/051,283 filed Feb. 4, 2005, which is a continuation of U.S. patent application Ser. No. 10/144,504 filed May 13, 2002, now U.S. Pat. No. 6,855,135, which is a Continuation-in-Part of U.S. patent application Ser. No. 09/994,537 filed Nov. 27, 2001, now U.S. Pat. No. 6,752,794, which is a Continuation-in-Part of U.S. patent application Ser. No. 09/725,352 filed Nov. 29, 2000, now U.S. Pat. No. 6,685,681, all of which are herein incorporated by reference.

BACKGROUND AND SUMMARY OF THE INVENTION

The present invention relates to bandages for wounds, and more particularly to the provision of bandages for use with a vacuum source.

The prior art contemplates that chronic wounds may be treated by providing a vacuum in the space above the wound to promote healing. A number of prior art references teach the value of the vacuum bandage or the provision of the vacuum in the space above the surface of a chronic wound.

A vacuum bandage is a bandage having a cover which seals about the outer perimeter of the wound and under which a vacuum is established to act on the wound surface. This vacuum applied to the wound surface causes healing of chronic wounds. Typically, suction tubes are provided for drawing away exudate from the wound, and this suction may be used to create the vacuum under the cover. If the cover is a flexible cover, which is typically more comfortable for the patient, some sort of porous packing may be provided under the cover to provide the space in which the vacuum is formed. The following U.S. Patents establish the nature of vacuum treatment bandages and devices: U.S. Pat. Nos. 6,095,992, 6,080,189, 6,071,304, 5,645,081, 5,636,643, 5,358,494, 5,298,015, 4,969,880, 4,655,754, 4,569,674, 4,382,441, and 4,112,947. All of such references are incorporated herein by reference for purposes of disclosing the nature of such vacuum treatment of wounds.

As shown, for example, in U.S. Pat. No. 5,645,081 (hereinafter the '081 patent), a method of treating tissue damage is provided by applying negative pressure to a wound. The negative pressure is provided in sufficient duration and magnitude to promote tissue migration in order to facilitate the closure of the wound. FIG. 1 of the '081 patent discloses an open cell polyester foam section covering the wound, a flexible hollow tube inserted into the foam section at one end and attached to a vacuum pump at another end, an adhesive sheet overlying the foam section and tubing to adhere to the skin surrounding the wound in order to form a seal that allows the creation of a vacuum when the suction pump is operating. The '081 patent further teaches use of negative pressure between about 0.1 and 0.99 atmospheres, and that the pressure can be substantially continuous, wherein the pressure is relieved only to change the dressing on the wound. Alternatively, the '081 patent teaches use of a cyclic application of pressure in alternating periods of application and non-application. In a preferred embodiment, pressure is applied in 5 minute periods of application and non-application.

Various other prior art references teach the value of the vacuum bandage or the provision of vacuum to the surface of a chronic wound. Several Russian language articles exist which establish the efficacy of vacuum therapy discovered in the 1980's. Examples of such prior art articles, each of which discusses the use of application of vacuum to a wound to promote healing, are as follows: "Vacuum therapy in the treatment of acute suppurative diseases of soft tissues and suppurative wounds", Davydov, et al., Vestn, Khir., September 1988 (the September 1988 article); "Pathenogenic mechanism of the effect of vacuum therapy on the course of the wound process", Davydov, et al. Khirurigiia, June 1990 (the June 1990 article); and "Vacuum therapy in the treatment of suppurative lactation mastitis", Davydov, et al. Vestn. Khir., November 1986 (the November 1986 article).

The Russian articles distinguish wound drainage from the use of vacuum therapy for healing. The Russian authors report that vacuum therapy resulted in faster cleansing of the wound and more rapid detoxification than with the traditional incision-drainage method. The November 1986 Russian article describes the vacuum therapy techniques as a reduction of 0.8-1 atmosphere for 20 minutes at the time of surgery, and subsequent 1.5 to 3 hour treatments at a reduced pressure of 0.1 to 0.15 from atmosphere, twice daily. These Russian articles teach the use of negative pressure to effect healing. The articles describe using several sessions per day, each lasting up to one hour, with a vacuum of 76-114 mmHg. The Russian articles teach using this vacuum method to decrease the number of microbes in the wound. The June 1990 article teaches that this vacuum therapy provides a significant antibacterial effect. The article describes the stepped up inflow of blood to the zone around the wound to lead to an increase in the number of leukocytes reaching the focus of inflammation. Subsequent articles and patents further develop the benefits obtained with vacuum therapy. The prior art, therefore, teaches the benefit and value of a vacuum bandage.

According to the present disclosure, a thin, flexible member for use in a vacuum bandage is provided. The member includes a wound contacting surface configured to be in contact with and conform to a wound surface of a wound. The member further includes a plurality of discrete holes formed in the wound contacting surface, a port which communicates with the vacuum source, and communicating means between the holes and the port. The member is made from a generally non-compressible material. Further, the material is generally transparent and non-porous.

In some illustrative embodiments, the communicating means comprises a plurality of distinct passageways between each hole and the port. The member includes a wound contacting layer having channels formed therein and a cover coupled to the wound contacting layer. The cover cooperates with the wound contacting layer, and the channels formed therein, to define the passageways. The member further includes a boss positioned near the port of the cover to prevent an upper surface of the wound contacting layer from sealing off the port of the cover when vacuum is applied to the port.

In some illustrative embodiments, the wound contacting surface of the member includes spacers contacting the wound to define a suction space between the member and the wound surface. The wound contacting surface may also be textured or roughened for contact with the wound surface. The unevenness of the textured or roughened surface provides communication of the negative pressure across the wound surface.

In some embodiments, the spacers and suction space are defined by a plurality of channels formed in the wound contacting surface. Each of the channels formed in the wound contacting surface opens toward the wound surface and includes side edges contacting the wound.

In some embodiments of the invention, the dressing member has such a plurality of channels formed in patterns on both of the wound contacting surface and the opposite surface and the plurality of holes provide communication between the channels on both surfaces. In some embodiments, the channel patterns on both surfaces are congruent or superimposed with both patterns radiating outwardly from the port and with the holes spaced radially along the channels.

In some embodiments, the dressing member is made from a material which is to be trimmed conformingly to fit the wound. In some embodiments, the dressing member is relatively transparent such that the condition of the wound surface can be observed through the wound member.

There is provided, therefore, a dressing for a wound, the dressing comprising a relatively thin flexible member which can be trimmed conformingly to fit the wound surface. A suction and irrigation port is associated with the dressing member, and a plurality of channels or passageways is formed in the member leading away from the port to provide communication between the port and areas of the wound surface. The dressing member is provided with a plurality of through holes in communication with the channels. A packing may be placed over the flexible member and a sealing film may be placed over the packing to seal around the perimeter of the wound to provide an enclosed space above the member in which a vacuum is formed by suction on the port. It will be appreciated, however, that some caregivers may choose to leave packing out of the bandage and have the sealing film placed directly over the flexible member. It has been found that some bandages function quite well without packing. Also, visual observation is improved without the packing. Irrigation fluid may be introduced to the port to impinge upon the wound surface and this fluid and wound exudate is removed from the space between the wound and the bandage member by suction applied to the port. It will be appreciated that the vacuum therapy and the irrigation therapy may take place without removal of the bandage. The illustrative member with the downwardly opening channels or spacers on the wound contacting surfaces provides a suction space which will uniformly apply the vacuum and the irrigation to the surface of the wound bed.

The covered channels on the opposite surface and the holes through the member further contribute to the ability to uniformly apply the vacuum therapy and irrigation fluid to the wound surface. A relatively large portion of the wound surface will be exposed to the vacuum therapy and irrigation using the illustrative bandage member. A large number of redundant passageways are provided for communicating from the access port directly to the wound surface. While some of the passageways may become blocked by exudate particles from the wound surface, other passageways will remain open for suction and irrigation.

The illustrative bandage, therefore, provides a relatively thin, flexible, comfortable bandage member which can be trimmed generally conformingly to fit into a wound bed and apply vacuum therapy and irrigation uniformly to the wound surface. The illustrative covered channel passageways on the opposite (upper or outer) surface provide a multitude of clearly defined passageways leading from the access port to the through holes leading directly into the suction space under the member.

In further embodiments, the member includes a connecter coupled to the cover for communication with the port of the cover. The connecter is configured for communication with the vacuum source and defines a right-angled passageway to provide a horizontal tube attachment.

In yet another embodiment, the member further includes an outer adhesive perimeter. This perimeter is configured to seal about the wound to a patient's healthy skin surrounding the wound. In another embodiment, the member further includes a wire form to permit a user or caregiver to mold or shape the member to fit the particular shape of a wound. In one embodiment, the wire form is molded into the cover and in another embodiment the wire form is molded into the wound contacting layer.

In still another embodiment, the member further includes a plurality of irrigation passageways configured for communication with an irrigation source and with the wound surface. The irrigation passageways are distinct from the passageways described above which are configured for communication with the vacuum source. The member further includes an irrigation port in communication with the irrigation passageways and configured for communication with the irrigation source. An irrigation layer is provided and includes channels formed therein which define the irrigation passageways.

A wound bandage for use on a chronic wound located on a patient's heel is also disclosed. In this embodiment, the member is saddle-shaped and includes an upper portion, a lower portion, and a neck portion coupled to and positioned between the upper portion and the lower portion. The saddle-shaped member is foldable into a configuration that cups the patient's heel. An embodiment having a member with a generally "V-shaped" cross-section is provided for use with sternal or abdominal wounds. The V-shaped member includes a right wing and a left wing coupled to the right wing. Further, the V-shaped member includes a central passageway in communication with the port of the cover and a plurality of lateral passageways in communication with the central passageway.

Another alternative member is disclosed for use with tunneled wounds. This member includes a truncated cone-shaped portion, a tube-shaped portion coupled to the cone-shaped portion, and a dome-shaped portion coupled to the tube-shaped portion. The port is positioned in the cone-shaped portion. Yet another member is disclosed which is dome-shaped and has a convex wound contacting surface.

A method of forming a member of a wound bandage is further provided in accordance with the present disclosure. The method includes the steps of molding a cover from a semi-cured silicone and the step of heat-sealing the cover to a wound contacting layer. In illustrative embodiments, the method further includes providing a connecter and heat sealing the connecter to the cover. In further embodiments, the method includes molding the connecter and the wound contacting layer from fully-cured silicone.

Additionally, a method of treating an open wound having a wound surface is provided in accordance with the present disclosure. The method includes the steps of providing a flexible member fabricated from non-porous material to have a wound contacting surface with holes in the surface, a port configured to communicate with a vacuum source, and passageways providing communication between the holes and the port. The method further includes placing the member into contact with the wound to functionally and physically interface with the wound surface and connecting the port to a vacuum source to provide suction at each of the holes. In illustrative embodiments, the method further includes the step of covering the wound and the member adjacent the wound to provide a space in which a vacuum is established by the vacuum source. In other embodiments, the method includes the step of irrigating the wound surface by connecting the port to a source of irrigation fluid expelled through the holes onto the wound surface.

Another alternative member is provided including a single stand-off coupled to the wound contacting or wound facing surface of the member. The stand-off includes a plurality of interconnected portions. Illustratively, the stand-off forms a spider-web-like design having a circle portion and a plurality of radial arms extending outwardly from the circle portion. Further illustratively, the stand-off includes an arc portion spaced-apart from and concentric with the circle portion. The radial arms extend through the arc portion. The cross-section of the stand-off is in the shape of a semi-circle having a radius of approximately 1.56 mm. The stand-off defines encompassed regions of the wound facing surface of the member.

Features of the invention will become apparent to those skilled in the art upon consideration of the following detailed description of preferred embodiments exemplifying the best mode of carrying out the invention as presently perceived.

BRIEF DESCRIPTION OF THE DRAWINGS

The detailed description particularly refers to the accompanying figures in which:

FIG. 1 is a part perspective, part diagrammatic view of a wound care bandage showing the wound care bandage located on the leg of a patient and coupled to both a vacuum and an irrigation source through the use of a switch valve;

FIG. 2 is a top view of a member of the wound care bandage showing the member including a vacuum/irrigation port, a plurality of channels radiating outwardly from the port, and through holes which extend through the member;

FIG. 7 is a sectional view of the bandage within the wound of the patient showing the wound surface, the wound contacting surface of the member adjacent the wound surface, the cover adjacent the opposite surface of the member, the tubing coupled to the port of the member, packing, and the outer film coupled to the patient's healthy skin to seal the environment;

FIG. 8 is another embodiment showing an alternate wound contacting surface of the member including spacers for contacting the wound surface to form an open space between the member and the wound surface;

FIG. 9 is a sectional view taken along line 9-9 of FIG. 8 showing one spacer and a through hole of the alternate member;

FIG. 10 is another embodiment showing an another wound contacting surface of the member including spacers or oblong ridges provided to form an open space between the member and the wound surface when the member is placed in the wound;

FIG. 11 is a sectional view taken along line 11-11 of FIG. 10 showing one oblong ridge and through hole of the alternate member;

FIG. 12 is another embodiment showing a wound care bandage having two ports;

FIG. 13 is another embodiment showing an alternate opposite surface of the member having ridges radially spaced around the port to provide a means of flow for exudate being vacuumed from the wound and/or for liquid being dispensed to the wound through the port;

FIG. 14 is a sectional view taken along line 14-14 of FIG. 13.

FIG. 15 is yet another embodiment showing a bandage having a plurality of ports each coupled to a vacuum/irrigation tube to provide an evenly distributed suction force across the member;

FIG. 23 is a top view of a member showing the member being saddle-shaped for use on a heel, as shown in FIG. 25, for example, and also showing a centrally located connecter coupled to the cover and in communication with a central port of the cover and channels of the wound contacting layer radiating outwardly from the port;

FIG. 24 is a top view of another member, similar to the embodiment of FIG. 23, showing the member being saddle-shaped, a port positioned on an upper portion of the member, and lateral passageways of the member extending outwardly and downwardly from a vertical central passageway of the member;

FIG. 25 is a perspective view of the member shown in FIG. 24 positioned around the heel of a patient's foot;

FIG. 26 is a perspective view of another embodiment of the member showing the member having a truncated cone-shaped portion coupled to a tube-shaped portion for use with tunneled wounds, as shown in FIG. 27;

FIG. 27 is a sectional view of the member shown in FIG. 26 showing the member positioned within the tunneled wound of a patient;

DETAILED DESCRIPTION OF THE DRAWINGS

A wound care bandage 10 is provided for use with a vacuum and irrigation source 12, 14, respectively, as shown in FIG. 1. An illustrative vacuum and irrigation source 12, 14 is disclosed in application Ser. No. 09/725,666 filed on Nov. 29, 2000 and application Ser. No. 09/369,113 filed Aug. 5, 1999. These pending applications, which are each owned by the assignee of this present application, are specifically incorporated herein by reference.

Bandage 10 promotes the healing of a large wound 16 (shown in FIGS. 3 and 7) by providing vacuum therapy to the wound 16 to promote blood flow and remove exudate from a wound surface 18 of the wound 16 and by providing for irrigation of the wound 16 with fluids such as saline, for example.

Figure 3:
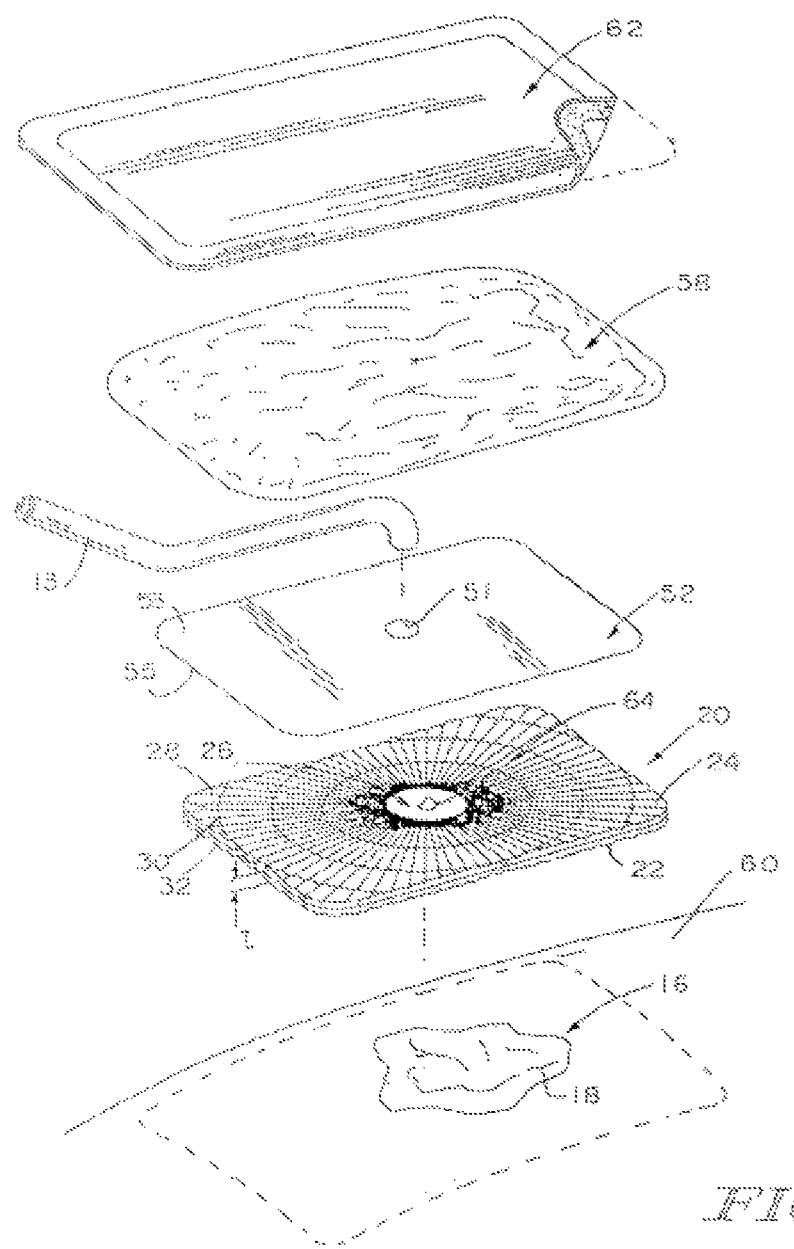
FIG. 3 is an exploded view of one embodiment of the wound care bandage showing the member having a wound contacting surface and an opposite surface, a cover adjacent the opposite surface, tubing which connects to the port of the member at one end and to the vacuum and irrigation sources at another end, packing to be placed on top of the tubing and member, and a sealing film which closes and seals the bandage to allow a vacuum environment to be created.

As shown in FIG. 3, wound care bandage 10 comprises a thin, flexible wound dressing member 20, shown in FIG. 2. Member 20 is made of a medical grade silicone or other type of elastomer which is pliable. Two companies, for example, which manufacture such medical grade silicone are GE Silicones and NuSil Technology. It is within the scope of this disclosure, however, to include a wound dressing member made of any type of thin, flexible material that is non-porous and non-foam-like. This thin, flexible material is also generally non-absorptive. For example, materials such as polyvinylchloride (PVC), PVC free of diethylhexyl phthalate (DEHP-free PVC), polyurethane, or polyethylene may be used in the manufacture of member 20.

Further, member 20 may be molded to include anti-microbial constituents. For example, it is within the scope of this disclosure to impregnate member 20 with silver ions which are known anti-microbials. The following PCT publications illustrate the use of anti-microbials in various products and are incorporated herein by reference: "Anti-microbial Plastic Closures for Drinking Containers", WO 00/26100; "Antimicrobial Contact Lens Case", WO 00/038552; "Antimicrobial Fabric and Medical Graft of the Fabric", WO 00/32247; "Antimicrobial Suturing Ring for Heart Valve", WO 00/30567.

Member 20 is also made of a generally non-adhesive material. Therefore, wound contacting layer 22, which lies adjacent to the wound surface 18, does not adhere to the wound surface 18. Further, member 20 is solid in nature and generally non-compressible. For example, when a negative pressure is applied to member 20, a thickness, t, of member 20, as shown in FIG. 3, remains relatively constant.

Figure 4:
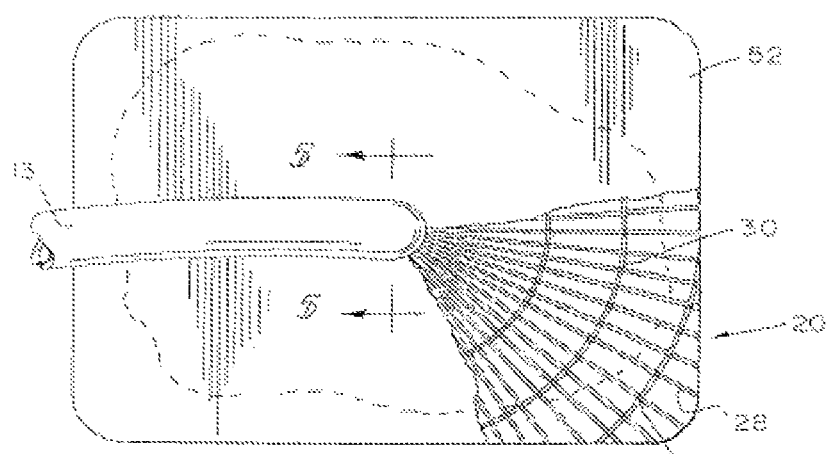
FIG. 4 is a top view of a portion of the bandage showing the cover with portions broken away and showing the member and the channels of the member enclosed by the cover in order to form passageways extending away from the port.
Figure 6:
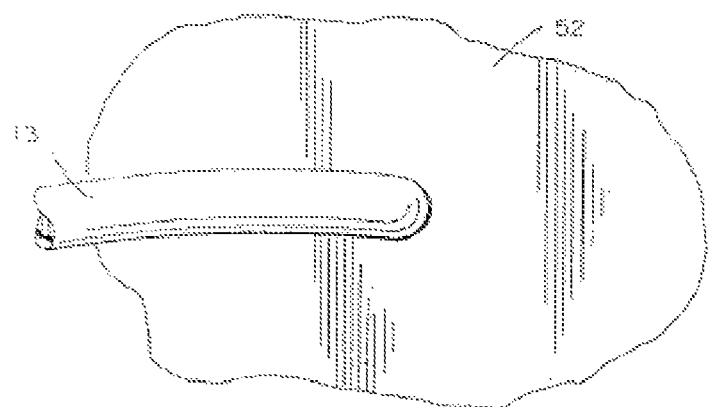
FIG. 6 is a top view of the portion of the member and cover shown in FIGS. 4 and 5 after having been trimmed to fit the particular wound of the patient.

As shown in FIG. 2, wound dressing member 20 is illustratively rectangular in shape. However, it is within the scope of the this disclosure for member 20 to be any suitable shape, some illustrative examples of which are described below in FIGS. 23-31. Further, member 20 may be cut to fit any size wound 16, as shown in FIGS. 4 and 6. Member 20 is illustratively molded with a thickness of 0.080 inches (2.032 mm). Illustratively, member 20 is made from a silicone of a Durometer 10A which is flexible. It will be appreciated that the channels or passageways formed in the member, as described below, will further contribute to its flexibility.

Figure 5:
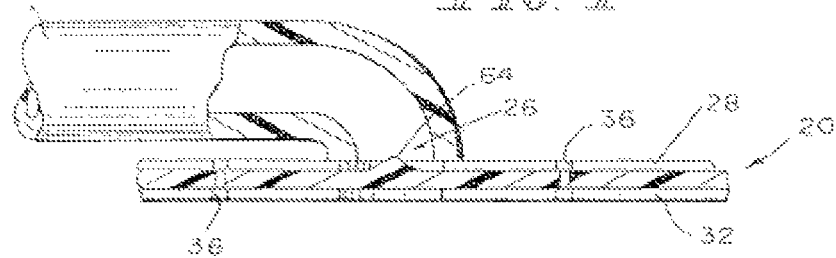
FIG. 5 is a sectional view taken along line 5-5 of FIG. 4 showing the tube which may be sealed to the port, showing a shallow cone of the port, and also showing the channels of the opposite surface and channels of the wound contacting surface and the holes which communicate between the channels.
Figure 16:
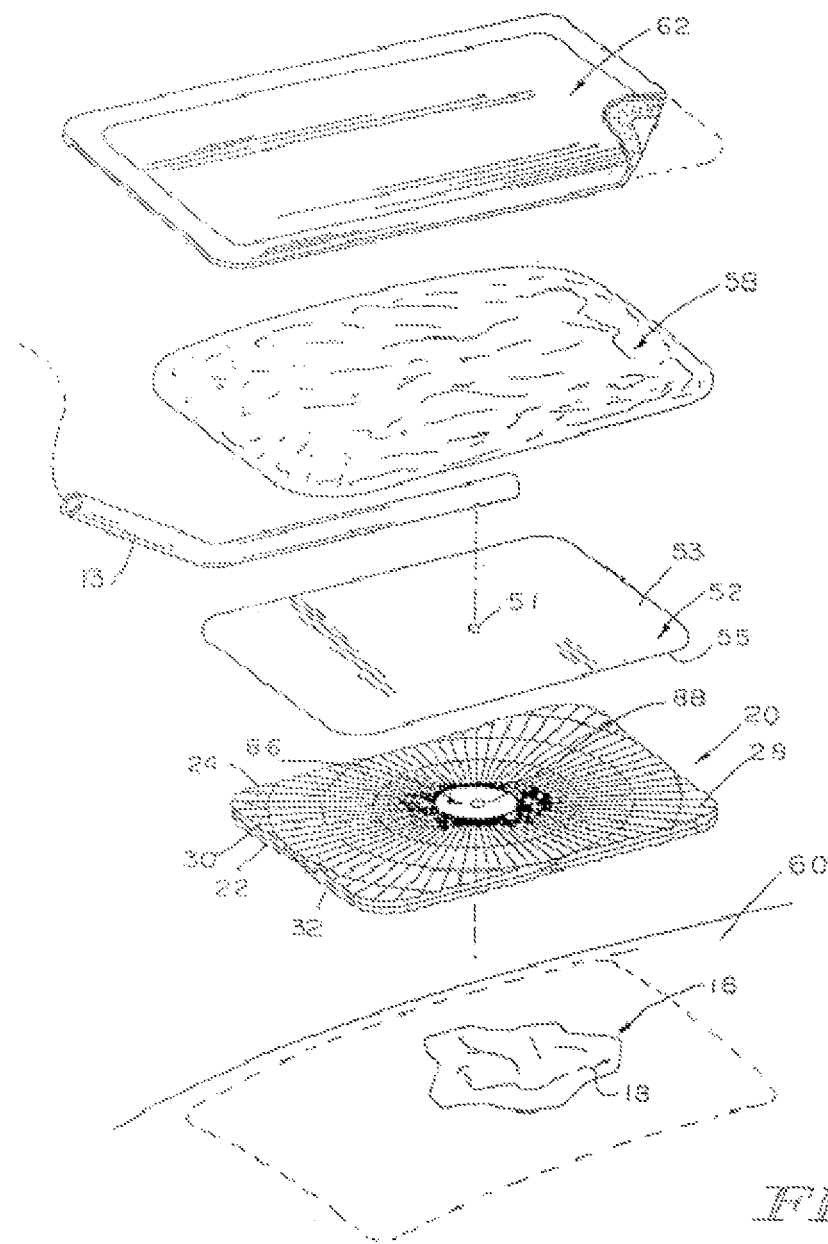
FIG. 16 is another embodiment showing a member of the bandage having a central aperture at the port of the member and channels extending radially outwardly from the central aperture.

Member 20 includes a wound contacting surface 22 and an opposite surface 24. Wound contacting surface 22 or portions thereof contact the wound surface 18 as shown in FIG. 7. Looking to FIG. 2, it can be seen that opposite surface 24 includes a central area defining a vacuum/irrigation port 26. A plurality of channels 28 are formed in opposite surface 24 and extend radially away from central area or port 26. Illustratively, each channel 28 is 0.030 inches (0.762 mm) wide and 0.030 inches (0.762 mm) deep. It is within the scope of this disclosure, however, to include channels 28 of member 20 having various widths and depths suitable for the present application. Port 26, as shown in FIG. 5, includes a shallow cone 64 in order to induce fluids dispensed through a vacuum/irrigation tube 13 from the vacuum and irrigation sources 12, 14 to flow evenly into channels 28. In an alternate embodiment shown in FIG. 16, an alternate port 86 includes an aperture 88 formed through member 20. In the FIG. 16 embodiment, the port communicates directly with the suction/irrigation space between the member 20 and the surface of the wound.

Vacuum/irrigation tube 13 is in communication with central area or port 26 of member 20 via a port 51 of a cover 52 (described below) of the bandage 10 coupled to the port. The tube 13 may be molded as part of the member 20 or attached to the member by welding, adhesion or other known techniques. The tube is preferably made of silicone, however, it is within the scope of this disclosure to include a vacuum/irrigation tube made of other medically suited materials. Opposite surface 24 further includes channels 30 which are concentric with port 26, as shown in FIG. 2. Concentric channels 30 have the same width and depth as that of channels 28 described above.

Wound contacting surface 22 includes a plurality of channels 32 which radiate outwardly from the center of member 20 similar to channels 28 of opposite surface 24. Similarly, wound contacting surface 22 also includes a plurality of channels 34 concentric with the center of member 20. Each channel 32, 34 of wound contacting surface 22 opens toward the wound surface 18 and includes outer edges 42 which contact the wound surface 18 or which act as spacers to provide space between the member 20 and the wound surface. Illustratively, the channels 32,34 of wound contacting surface 22 have the same dimensions as the channels 28, 30 of opposite surface 24. In other words, illustratively channels 32, 34 of wound contacting surface 22 are 0.030 inches (0.762 mm) deep and 0.030 inches (0.762 mm) wide. However, it is within the scope of this disclosure to include channels 32, 34 of surface 22 having other widths and depths.

Through holes 36 are provided in member 20 for communication between the channels 28, 30 of the opposite surface 24 with the channels 32, 34 of the wound contacting surface 22. As shown in FIG. 2, holes 36 are illustratively positioned to lie within concentric channels 30, 34 of each respective surface 22, 24 of member 20. Holes 36 are illustratively 0.030 inches (0.762 mm) in diameter and are illustratively spaced approximately 0.500 inches (12.700 mm) apart along channels 28, 30, and 32, 34 of each respective surface 22, 24. Member 20 is provided in small, medium, and large sizes. The small sized member has a length of 3.00 inches (76.20 mm) and a width of 4.00 inches (101.60 mm); the medium sized member has a length of 4.00 inches (101.60 mm) and a width of 6.00 inches (152.40 mm); the large sized member has a length of 6.00 inches (152.40 mm) and a width of 10.00 inches (254.00 mm). The holes of the small and medium sized members 20 are 0.030 inches (0.762 mm) in diameter. The large sized member, however, includes some holes having a diameter of 0.030 inches (0.762 mm) and other holes having a diameter of 0.040 inches (1.016 mm). It is, however, within the scope of the disclosure to include members of other suitable shapes and sizes including holes having other suitable size diameters and other spacing as well.

Channels 32, 34 of wound contacting surface 22 provide open spaces 40 between the wound surface 18 and member 20, as shown in FIG. 7. Open spaces 40 are defined by each channel 32, 34 of wound contacting surface 22, each outer edge 42 of channels 32,34, and wound surface 18. Each through hole 36 of member 20 opens into the open spaces 40 formed by channels 32, 34. Open spaces 40 allow vacuum source 12 to establish a generally uniformly distributed vacuum therapy to draw exudate from the wound 16 into the channels 32, 34 of wound contacting surface 22.

It is within the scope of this disclosure to provide spacers 46, for example, shown in FIGS. 8 and 9. Spacers 46 protrude outwardly from wound contacting surface 22 to contact wound surface 18. Open spaces 40 are provided between spacers 46. As shown in FIG. 9, each spacer 46 has an illustrative depth of approximately 0.030 inches (0.762 mm). However it is within the scope of this disclosure to include spacers having other suitable dimensions which provide open spaces 40. As with member 20 including channels 32, 34 on wound contacting surface 22, holes 36 of member 20 including spacers 46 are positioned to open into the open spaces 40.

Further, it is within the scope of this disclosure to include member 20 having other types of spacers on wound contacting surface 22 which create open spaces 40 when wound contacting surface 22 is adjacent the wound surface 18. In another embodiment, as shown in FIGS. 10 and 11, oblong ridges 50 are provided on wound contacting surface 22. Ridges 50 are similar in shape and function to spacers 46. Ridges 50 protrude away from member 20 and contact wound surface 18 when member 20 is place on wound surface 18 to provide open spaces 40 between wound surface 18 and member 20 to establish a generally uniform vacuum across the wound surface 18. As shown in FIG. 11, each ridge 50 illustratively has a preferred depth of 0.030 inches (0.762 mm), however, a ridge having other suitable dimensions is within the scope of this disclosure. As illustrated by channels 32,34 of wound contacting surface 22, spacers 46, or ridges 50, it is within this disclosure to include other structures which acts as spacers to create open spaces 40 between the wound surface 18 and member 20 when member 20 is placed on the wound surface 18 to distribute suction and irrigation generally uniformly throughout the wound 16. For example, the wound contacting surface maybe textured or roughened as illustrated by irregular nubs 74 in FIGS. 21 and 22. This textured surface is described in more detail below with respect to a bandage 11 shown in FIG. 17.

As mentioned above, bandage 10 further comprises cover 52 for covering and coupling to opposite surface 24 of member 20. Port 51 of cover 52 communicates with central area or port 26 of member 20 and channels 28 of member 20. Cover 52 is provided to cover channels 28, 30 of opposite surface 24. Cover 52 and channels 28 of opposite surface 24 cooperate to form passageways 56, as shown in FIG. 7, extending away from port 26. Passageways 56 are also formed by the cooperation of concentric channels 30 of opposite surface 24 and cover 52. Cover 52 is adhered to member 20 through the use of an adhesive or other suitable means such as heat sealing, for example, which is described in more detail below. It will be appreciated that the covered channels 28, 30 provide an ideal way to fabricate a multitude of passageways 56 communicating with the wound surface. In an alternate embodiment, passageways 56 are formed by cooperation of ridges 54 on opposite surface 24 of member 20, rather than channels 30, and cover 52, as shown in FIGS. 13 and 14, for example. It is within the scope of this disclosure to include a bandage 10 forming other passageways 56 extending away from port 26. Holes 36 of member 20 having ridges 54 are located within passageways 56 of bandage 10 similar to holes 36 of member 20 having radial channels 28 and concentric channels 30.

It will be appreciated that the illustrative cover 52 may be provided with scale marking for gauging the wound size or healing progress. Circular markings may be added at 0.5 cm or 1.0 cm intervals, for example, to provide convenient measuring of the wound and healing progress.

As shown in FIGS. 3 and 7, bandage 10 further includes gauze or other suitable packing 58 which lies on top of cover 52 and is provided to fill the wound 16 up to the surface of the patient's healthy skin 60. As noted above, such packing 58 may be optional with the caregiver. A sealing film 62 of bandage 10 is placed over packing 58. Film 62 is provided to cover the entire wound 16 and to extend across and attach around tube 13 to the patient's healthy skin 60, as shown in FIGS. 1 and 7. Preferably, film 62 is an occlusive or semi-occlusive material which allows water vapor to permeate through. Because of this characteristic, the film 62 is referred to as Moisture Vapor Transmission Rate film or MVTR film. The products Tegaderm™, made by 3M, and OpSite™ made by Smith and Nephew can be used for film 62, for example. The product OpSite™ is a semi-permeable film. Film 62 is approximately 0.003 inches (0.076 mm) thick, however, it is within the scope of this disclosure to include any occlusive or semi-occlusive film 62 having other thickness. Film 62 is provided to create a sealed environment below the film 62 and around the wound 16 in which a vacuum or negative pressure can be maintained as provided by vacuum source 12.

As shown in FIG. 7, vacuum/irrigation tube 13 or an extension added to the tube 13 extends over the edge of member 20 and cover 52 and out from under the edge of the sealing film 62. In use, irrigation source 14 delivers liquid through tube 13 and port 51 of cover 52 to port 26 and onto the top of a shallow cone 64 of member 20 which extends upwardly as shown in FIGS. 5 and 7. Cone 64 acts to spread the liquid out through the passageways 56 formed by the cooperation of channels 28, 30 (or ridges 54) and cover 52. The fluid moves radially out through passageways 56 to holes 36. The fluid then moved down through holes 36 to open spaces 40 to impinge on wound surface 18.

A switch valve 66 is illustratively provided, as shown in FIG. 1, to allow a user to switch between the use of the vacuum source 12 and the irrigation source 14. It will be appreciated that mechanism other than the switch valve 66 may be used selectively to couple the vacuum source or the irrigation source to the bandage. Simple tube clamps, for example, may be used selectively to open and close the tube set provided with the bandage 10. When valve 66 is switched to operate the vacuum source 12, the vacuum suction draws exudate into the open spaces 40 and up through the holes 36. The exudate is then drawn radially inwardly through passageways 56 toward port 26 and finally through tube 13.

Although illustrative bandage 10 includes one central port 51 of cover 52 and central area or port 26 of member 20, it is within the scope of this disclosure to include multiple ports 70, as shown in FIGS. 12 and 15, for example. Bandage 10 may make use of two ports 70 located at opposite ends of member 20, as shown in FIG. 12. Alternately, as shown in FIG. 15, bandage 10 may make use of a plurality of ports 70 spaced throughout member 20. It is contemplated that, in some embodiments having two ports, one port may be used for suction or vacuum therapy and the other port may be used for irrigation therapy.

It is contemplated that irrigation source 14 may be operated to provide irrigation fluid at various selected pressures. It is also contemplated that the bandage 10 and dressing member 20 may be provided in various sizes and shapes, some examples of which are shown in FIGS. 23-31 and are discussed below. The dressing member 20 may be reused with a single patient. It is also contemplated that the dressing 10 may be used with manual irrigation (where a nurse uses the syringe manually) as well as the powered syringe 14.

Referring now to FIGS. 17-22, there is shown another exemplary embodiment of a wound care bandage 11. Bandage 11 is somewhat similar to bandage 10. As such, the same reference numerals have been used to designate similar components to those components previously discussed in regard to FIGS. 1-7, and additional discussion thereof is not warranted. One difference between bandage 10 and bandage 11 is that a wound dressing member 19 of FIGS. 17-22 is defined as including the combination of a wound contacting layer 80, similar to member 20 of FIGS. 1-7, cover 52 coupled to layer 80, and a connecter 23 coupled to cover 52 for communication with vacuum source 12 and/or irrigation source 14. It is also within the scope of this disclosure for connecter 23 to be integrally coupled to cover 52.

Similar to member 20, member 19 is thin and flexible. Layer 80, cover 52, and connecter 23 are each made of a medical grade silicone or other type of pliable elastomer as described above with respect to member 20. Member 19 is similarly non-porous, non-foam-like, and generally non-absorptive. Materials such as PVC, DEHP-free PVC, polyurethane, or polyethylene may similarly be used in the manufacture of member 19. Further, layer 80, cover 52, and connecter 23 of member 19 may each be molded to include anti-microbial constituents similar to member 20.

Figure 18:
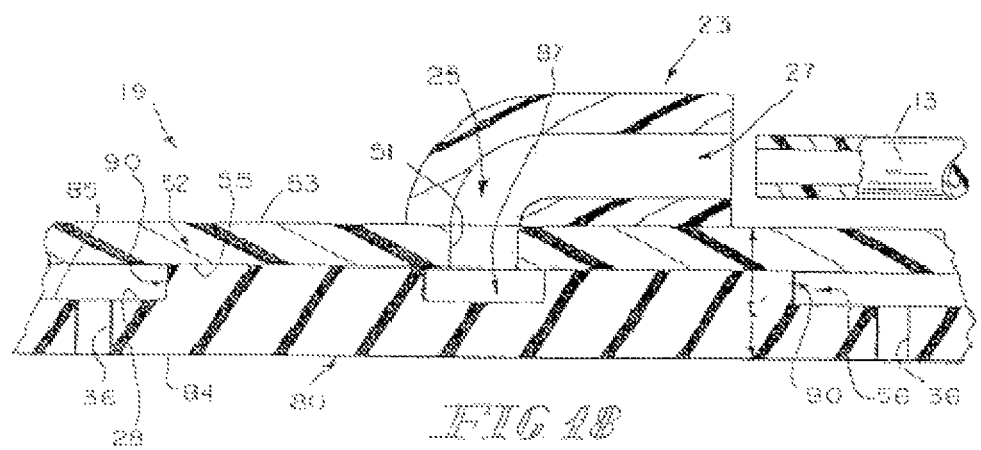
FIG. 18 is a sectional view of the member of FIG. 17 showing the non-porous nature of the member and also showing distinct passageways and through holes of the member.
Figure 19:
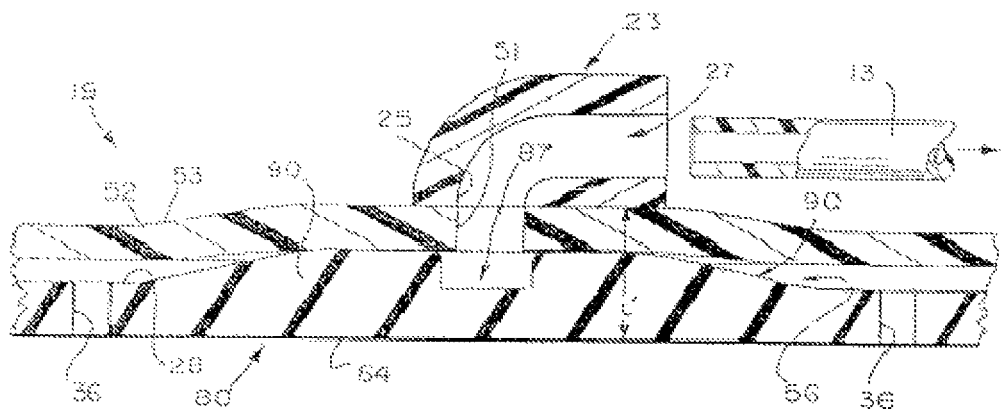
FIG. 19 is a sectional view similar to FIG. 18 showing rounded protrusions or bosses of the wound contacting layer adjacent to the cover and positioned about a port of the cover.
Figure 20:
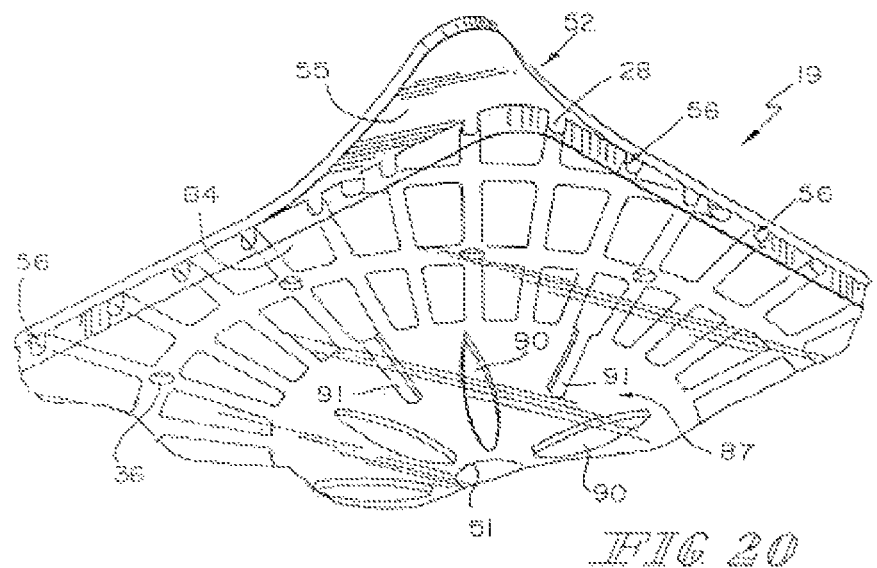
FIG. 20 is a bottom perspective view of the member showing a smooth wound contacting surface of the member and also showing the transparent nature of the member.

Also similar to member 20, member 19 is made of a generally non-adhesive material to prevent wound contacting layer 80, which lies adjacent to the wound surface 18, from adhering to the wound surface 18. Further, member 19 is similarly solid in nature and generally non-compressible. For example, when a negative pressure is applied to member 19, a thickness t', of member 19, as shown in FIGS. 18 and 19, remains relatively constant. Thickness, t', represents solid areas of member 19 where a channel or passageway is not present. Member 19 is generally pliable and .flexible, but is not generally compressible. Further, as shown in FIG. 20, member 19 (like member 20) is transparent to enable a caregiver to be able to see the wound 16 through member 19 when member 19 is placed adjacent to wound surface 18. This transparency allows the caregiver to view the progress of the healing of the wound 16.

Figure 17:
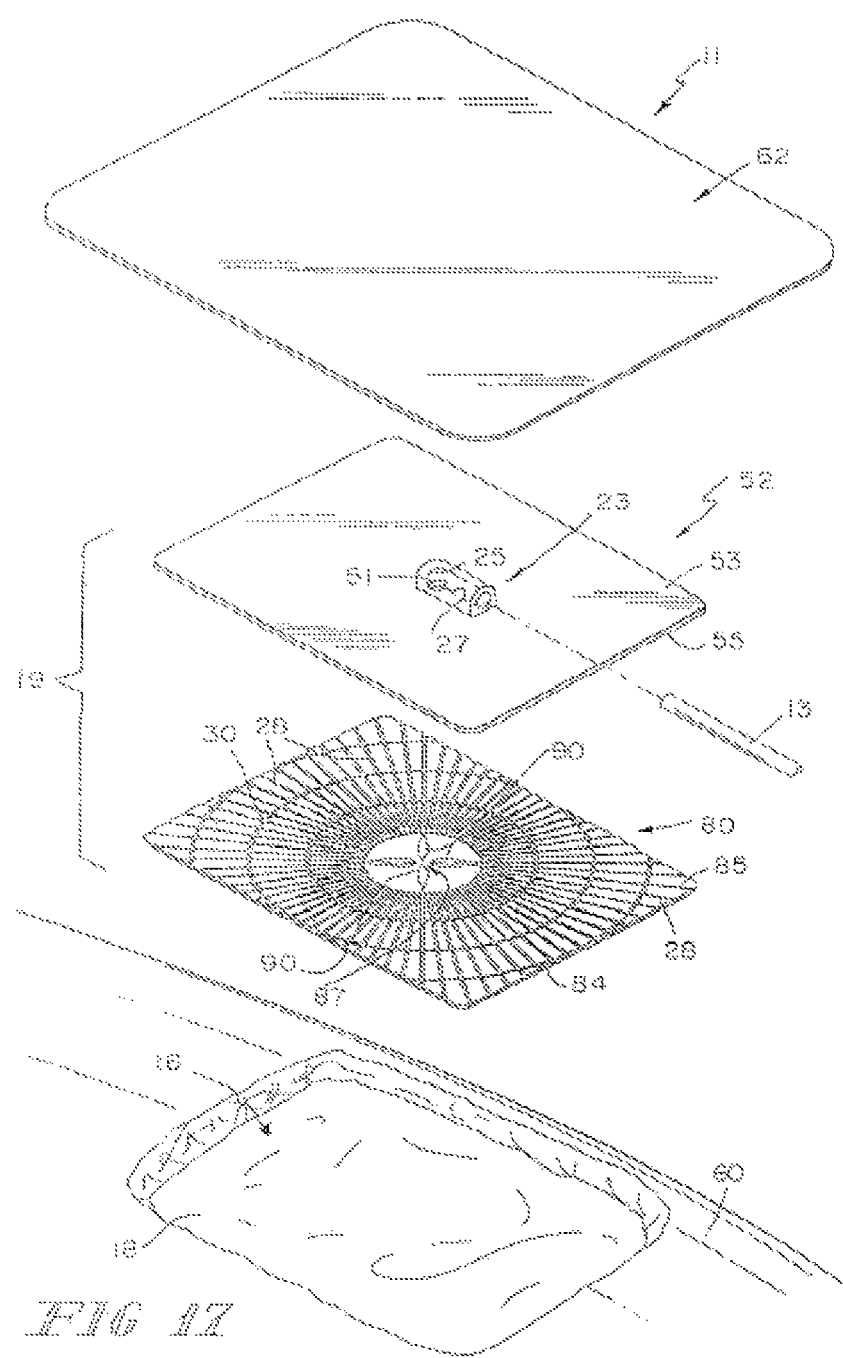
FIG. 17 is an exploded perspective view of another wound care bandage similar to the wound care bandage of FIG. 1 showing the bandage positioned above a wound bed and including a wound contacting layer and a cover of the bandage which cooperate to form a wound dressing member for placement within the wound bed, and also showing sealing film to cover the member and seal about the wound.

Layer 80 includes a wound contacting surface 84 and an upper or opposite surface 85. Wound contacting surface 84, or portions thereof, contacts and generally conforms to the wound surface 18. Opposite surface 85 includes a central area 87 and the same plurality of channels 28, shown previously in FIGS. 2-4 with respect to member 20. Channels 28 extend radially away from central area 87. Central area 87 is similar to central area or port 26 of a member 20 in that central area 87 communicates with port 51 of cover 52. However, central area 87 is recessed relative to the portions of upper surface 84 between channels 28, as shown in FIGS. 18 and 19. As shown in FIGS. 17 and 20, channels 28 are open at the sides and ends of member 19, similar to channels 28 of member 20. Opposite surface 85 further includes concentric channels 30, shown in FIGS. 17, 20 and 21. As shown in FIG. 17, central area 87 of layer 80 is provided to communicate with the vacuum source 12 and irrigation source 14 through cover 52, as will be described below.

A plurality of radially extending protrusions or bosses 90 are positioned around central area 87. Bosses 90 are positioned between central area 87 and channels 28, 30, as shown in FIG. 17. Bosses 90 prevent central area 87 from collapsing in on port 51 of cover 52 and forming an unwanted seal which would effectively block air flow through port 51 while suction is applied to bandage 11. Port 51 communicates with the vacuum source 12 and/or the irrigation source 14 via connecter 23 and tube 13, as shown in FIGS. 17-20. As mentioned above, port 51 is in communication with central area 87 of layer 80.

Illustratively, four bosses 90 are shown in FIG. 17. However, it is within the scope of this disclosure to provide any number of bosses 90, including eight bosses, or the like about central area 87 of layer 80 to prevent central area 87 from sealing off port 51 of cover 52 as suction is applied to bandage 11. Further, it is within the scope of this disclosure to include bosses 90 having a tapered cross-section, as shown in FIG. 19, or to include a boss or bosses having any shape that prevents central area 87 from sealing off port 51 when suction is applied to bandage 11.

Alternative or supplemental bosses 91 are shown in FIG. 19. Bosses 91 are positioned between bosses 90 and further prevent central area 87 from collapsing on port 51 and forming an unwanted seal blocking air flow through port 51 while suction is applied to bandage 11. Alternative bosses 91 are generally rectangularly shaped and extend inwardly from channels 28 toward central area 87.

Figure 32:
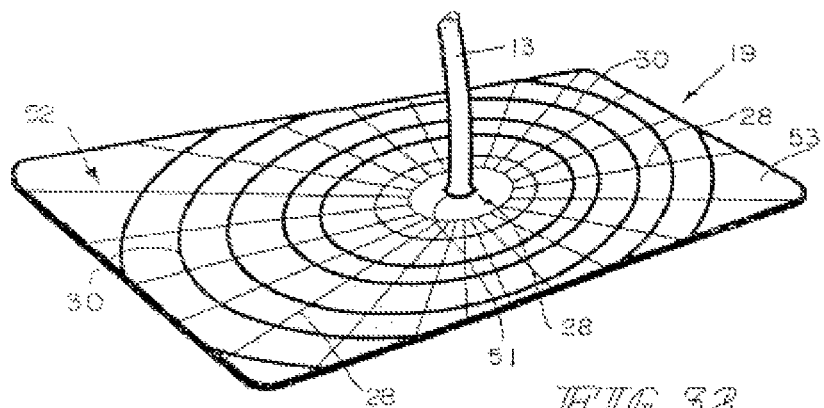
FIG. 32 is a perspective view of another embodiment of the bandage showing a vertical tube attachment at the port of the member.

Connecter 23, as shown in FIGS. 17-19, is a tubal port coupled to a top surface 53 of cover 52 and in communication with port 51 of cover 52. As mentioned before, it is within the scope of this disclosure for connecter 23 to be a separate component of member 19 which is coupled to cover 52 or for connecter 23 to be molded integrally with cover 52. Connecter 23 includes a passageway formed at a right-angle. Thus, the passageway in connecter 23 has a vertical portion 25 that communicates with port 51 and a horizontal portion 27 that communicates with vertical portion 25. Connecter 23 connects with tube 13 to provide a horizontal tube attachment with respect to port 51. A vertical tube attachment is shown in FIG. 32, for example. In FIG. 32, tube 13 is coupled directly to port 51 of cover 52. Cover 52 includes a bottom surface 55 and top surface 53, as shown in FIG. 17. Bottom surface 55 engages opposite surface 85 of layer 80, as shown in FIGS. 18-20.

In some embodiments, member 19 is made by heat sealing opposite surface 85 of layer 80 and bottom surface 55 of cover 52 together and by heat sealing connecter 23 to top surface 53 of cover 52. Member 20 of bandage 10 may also be heat sealed to cover 52. With respect to member 19 of bandage 11, for example, each of connecter 23, cover 52 (or the combination of cover 52 and connecter 23), and layer 80 may be pre-shaped and formed from semi-cured silicone. Once the connecter 23, cover 52, and layer 80 are placed together appropriately, the entire member 19 may be heated to heat seal and cure each of the three components to one another. Alternatively, for example, the cover 52 only may be made from semi-cured silicone while the connecter 23 and layer 80 may be made from fully cured silicone. Once placed together and heated, connecter 23 and layer 80 will heat seal to cover 52. Semi-cured silicon may be bought and pre-molded from a manufacturer such as NuSil Technology, for example. Although the method of heat sealing the cover 52, connecter 23, and layer 80 to each other is disclosed, it is within the scope of this disclosure to form member 19 by coupling layer 80, cover 52, and port 51 together by any other means such as through the use of adhesives, for example. Further, it is within the scope of this disclosure to provide a member 19 where cover 52 lies adjacent to, but is not coupled to, layer 80.

As mentioned above, cover 52 is coupled to layer 80 and connecter 23 is coupled to cover 52 to form member 19. Cover 52 and layer 80 cooperate to form distinct passageways 56 of member 19 defined by channels 28, 30 of layer 80 and bottom surface 55 of cover 52. Passageways 56 are in communication with central area 87 of layer 80 and central area 87 of layer 80 is in communication with port 51 of cover 52 which is in communication with the vacuum and/or irrigation sources 12, 14 via connecter 23 and tube 13. Therefore, passageways 56 are in communication with the vacuum and/or irrigation sources 12, 14.

Figure 21:
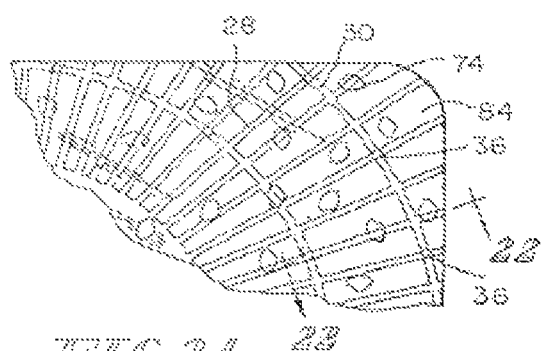
FIG. 21 is a bottom view of a portion of a member having a rough or textured wound contacting surface.
Figure 22:
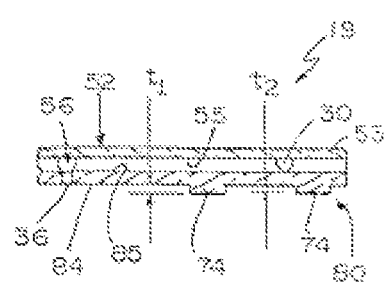
FIG. 22 is a sectional view taken along line 22-22 of FIG. 21 showing the irregular texturing of the wound contacting surface of the member.

Layer 80 (similar to member 20) includes through holes 36 which extend from channels 28, 30 through layer 80 to wound contacting surface 84, as shown in FIGS. 18 and 19. Holes 36 are distinct and are provided to communicate with channels 28, 30 of layer 80. Holes 36 therefore communicate with passageways 56 of member 19 and the vacuum and/or irrigation sources 12, 14 as well to allow the suction from the vacuum source 12 and/or the fluid from the irrigation source 14 to reach the wound surface 18 via the holes 36. As shown in FIGS. 2, 20, and 21, holes 36 have a staggered arrangement. Illustratively, holes 36 are 0.030 inches (0.762 mm) in diameter and are spaced approximately 0.500 inches (12.700 mm) apart along channels 28, 30 of layer 20. As mentioned before, however, it is within the scope of the disclosure to include holes having other suitable sized diameters and/or other suitable spacing that allow for the removal of exudate without clogging. For example, the small and medium sized bandages, as described above, each include holes having a diameter of 0.030 inches (0.762 mm) while the large sized bandage includes some holes having a diameter of 0.030 inches (0.762 0101) and other holes having a diameter of 0.040 inches (1.016 mm). Bandage 11 further includes sealing layer or film 62 that is placed over cover 52 and around tube 13, as shown in FIGS. 1 and 17 and described above with respect to bandage 10. Film 62 may be substantially larger than the wound 16 or member 19 to provide an effective seal about the member 19 and the wound 16. Bandage 11 does not include gauze or packing 58 included in bandage 10.

Illustrative member 19 of bandage 11 includes a smooth wound contacting surface 84, as shown in FIG. 17. Wound contacting surface 84 may also be textured or roughened as illustrated by irregular nubs 74 shown in FIGS. 21 and 22. Nubs 74 may have different dimensions as shown by thickness, t1, and thickness, t2, in FIG. 22. By providing member 19 with a textured or roughened surface, a space is created between surface 84 of layer 80 and wound surface 18. Through holes 36 communicate with this space which permits vacuum source 12 to establish a generally uniformly distributed vacuum or negative pressure to the wound surface 18 to draw blood from the body to the wound surface 18 and to draw exudate from the wound 16 through holes 36, into channels 28, 30 and passageways 56, and out port 51 of cover 52. It is within the scope of this disclosure to include other means for providing a space between surface 84 and wound bed surface 18 such as providing ribs, protrusions, channels, spacers, etc, as described above with respect to member 20 of bandage 10.

The vacuum or negative pressure which draws blood from the body to the wound surface 18 and draws exudate from the wound 16 up through member 19 promotes the healing of wound 16. As wound 16 heals, granulations form along the wound surface 18. Granulations, therefore, are the replacement within the wound bed of tissue lost. As the granulations fill in the wound bed causing the wound 16 to heal, member 19 rides up on the wound surface 18 on top of the granulations which are formed.

Figure 35:
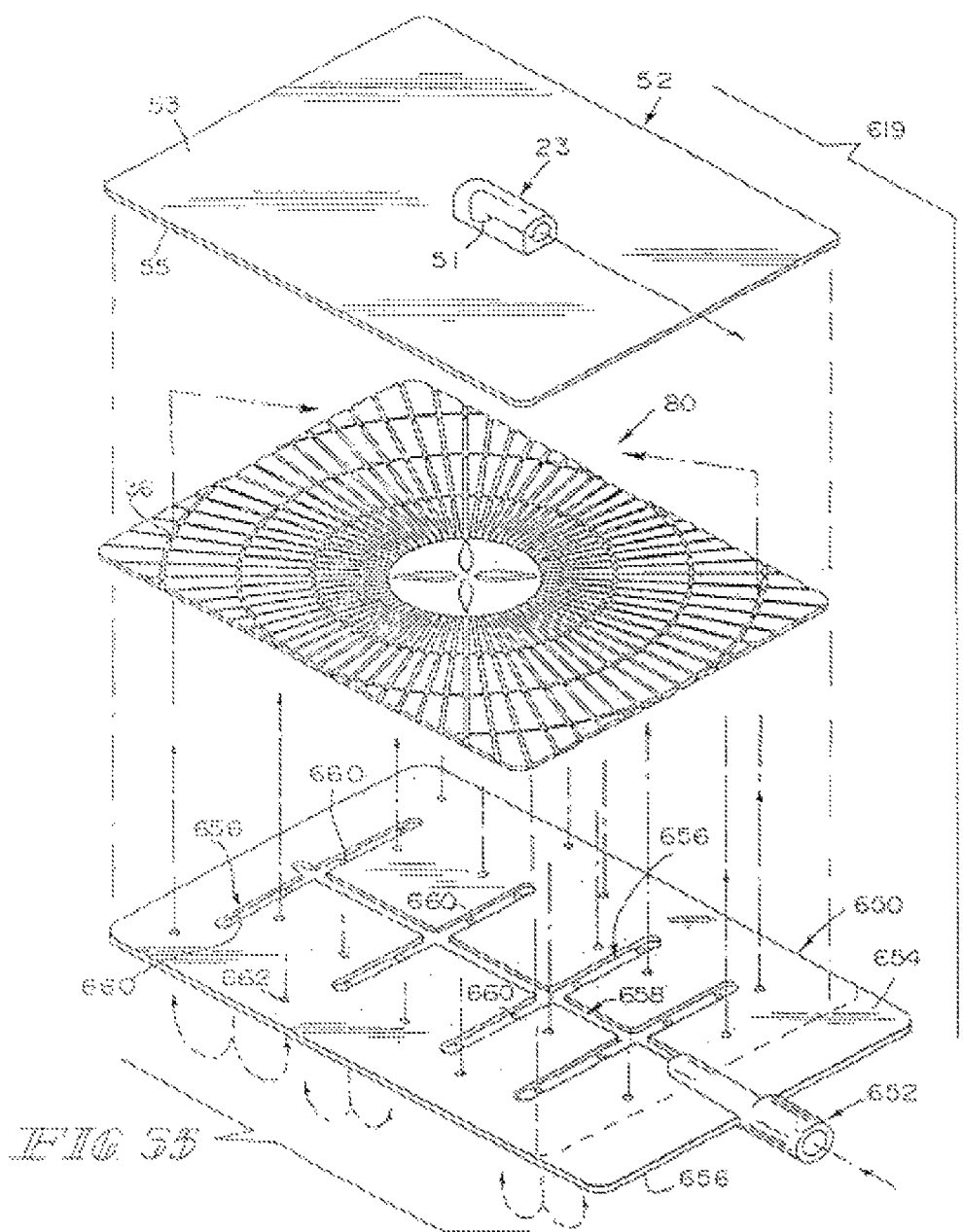
FIG. 35 is an exploded perspective view of another member showing the member including a cover, a wound contacting irrigation layer, and an intermediate layer positioned between the cover and the irrigation layer.
Figure 36:
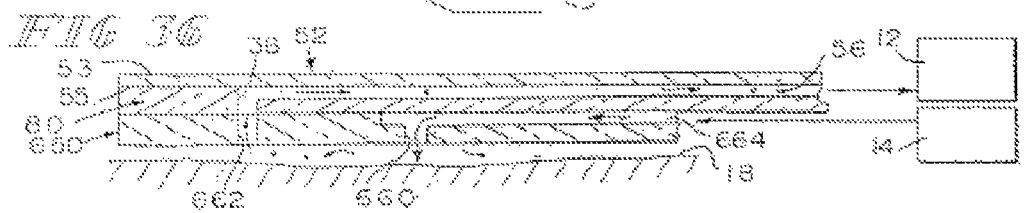
FIG. 36 is a sectional view of the member of FIG. 35 showing the irrigation layer in communication with an irrigation source (illustrated diagrammatically) and showing the cover in communication with a vacuum source (illustrated diagrammatically) to provide the member with the capability to simultaneously apply vacuum and irrigate the wound.

Although illustrative bandage 10 includes one central port 40, it is within the scope of this disclosure to include multiple ports. It is further within the scope of this disclosure to provide an illustrative member 619, as shown in FIGS. 35 and 36 and discussed below, having multiple ports and multiple passageway sets for use independent of each other.

Figure 41:
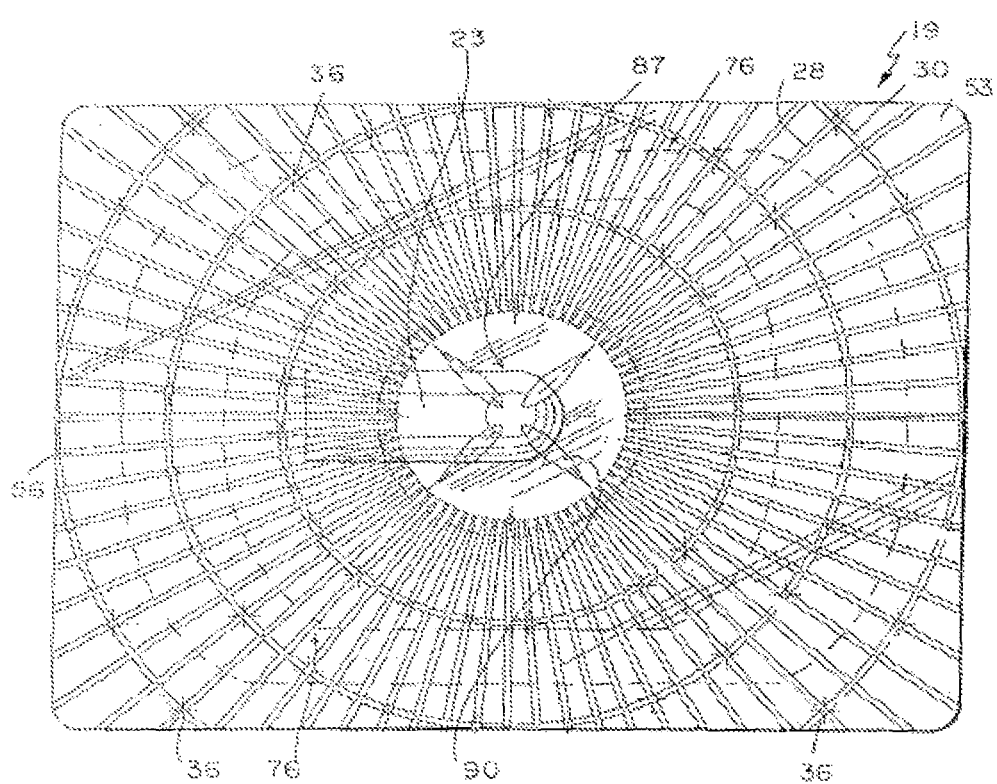
FIG. 41 is a top view of the member of the present invention showing the cover of the member including scale markings to provide a caregiver with a reference point for trimming the member to fit the particular wound of the patient.

In order to accommodate different sized wounds 16, member 19 may be trimmed to fit a particular wound 16. As shown in FIG. 41, some embodiments of member 19 include scale markings 76, indicated by the dotted lines. Scale markings 76 indicate areas where a caregiver may trim member 19 to fit a particular wound 16. Further, the scale markings 76 may denote measurement sizes, for example, to permit a caregiver to cut the member 19 to fit a pre-measured wound 16. Also, as mentioned above, the transparent nature of member 19 is illustrated in FIG. 41.

In order to accommodate various types and placements of wounds on patients, member 19 may be provided in various conforming shapes and sizes. For example, illustrative embodiments of a member 119 are shown in FIGS. 23-25 for use with a wound on a patient's heel 117. Member 119 is saddle-shaped and includes a top portion 150, a bottom portion 152, and a neck portion 154 integrally coupled to and spaced between top portion 150 and bottom portion 152, as shown in FIGS. 23 and 24. Member 119 includes a right and a left side 156, 158 which are each shaped to form an inwardly facing "W". Each W-shaped side 156, 158 includes a top point 160, a first trough 162, a peak 164, a second trough 166, and a bottom point 168. The neck portion 154 is positioned between each of the peaks 164.

Member 119 is similar to member 19 and includes a cover (not shown) and a wound contacting layer (not shown) having channels 28, 30 and through holes 36. To form member 119, the cover and layer are each saddle-shaped and include matching W-shaped sides. The cover and layer cooperate to form passageways 56 of member 119 in a manner similar to the manner in which cover 52 and layer 80 (and cover 52 and member 20) cooperate to form passageways 56 in member 19. All similar features between member 19 and alternate member 119 are marked with similar reference numerals. The cover of member 119 includes port 51 formed in top surface 53 of the cover and in communication with connecter 23.

Port 51 and connecter 23 are centrally located and passageways 56 radiate outwardly therefrom in the embodiment of FIG. 23. Illustratively, port 51 and connecter 23 are located on top portion 150 of member 119, the embodiment shown in FIG. 24. Passageways 56 of member 119 shown in FIG. 24 are defined by a central passageway 141 in communication with port 51 of the cover and lateral passageways 142 in communication with central passageway 141. The passageways 56 in the embodiment of FIG. 24 terminate before reaching the peripheral edge of member 119, whereas passageways 56 in the embodiment of FIG. 23 are open at the peripheral edge. As shown in FIG. 25, member 119 is folded to cup the patent's heel 117. In the illustrative cupped configuration of member 119, troughs 162 of top portion 150 overlap troughs 166 of bottom portion 152.

A member 219 is illustratively shown in FIGS. 26 and 27 and is used to treat tunneled wounds such as wound 116. Member 219 includes a truncated cone-shaped portion 250 and a tube-shaped portion 252 coupled to cone-shaped portion 250 at a first end 254. A dome-shaped tip 256 is coupled to tube-shaped portion 252 at a second end 258 of the tube-shaped portion 252.

Member 219 is similar to members 119 and 19 in that member 219 includes a wound contacting layer 220 coupled to a cover 222. Further, wound contacting layer 220 and cover 222 cooperate to form passageways 56 which communicate with port 51 of cover 222 and connecter 23. Wound contacting layer 220 is formed to define through holes 46 which communicate with the passageways 56 of member 219 and with wound bed surface 18 of tunneled wound 116.

Member 219 operates in the same or similar manner as members 119 and 19 in that connecter 23 may be coupled to a vacuum source 12 for establishing a vacuum about the wound bed surface 18 to draw blood up to the wound bed surface 18 and/or to remove exudate from the wound bed surface 18. Connecter 23 may also be coupled to irrigation source 14 to supply fluids such as saline, for example, to the wound bed surface 18. As shown in FIGS. 26 and 27, port 51 and connecter 23 of member 219 are positioned on the cone-shaped portion 250. However, it is within the disclosure to position port 51 and connecter 23 anywhere on member 219.

Figure 28:
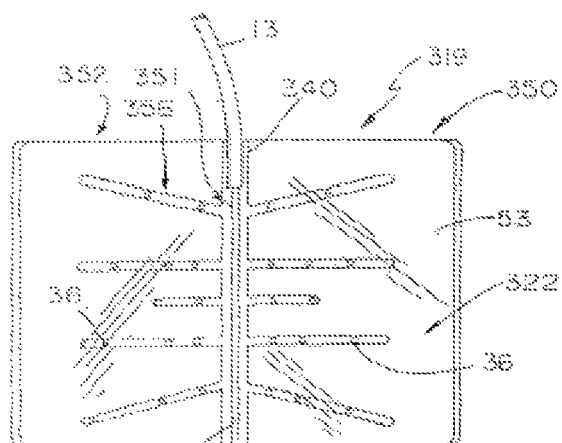
FIG. 28 is a top view of a "V-shaped" member for use with sternal or abdominal wounds, for example.
Figure 29:
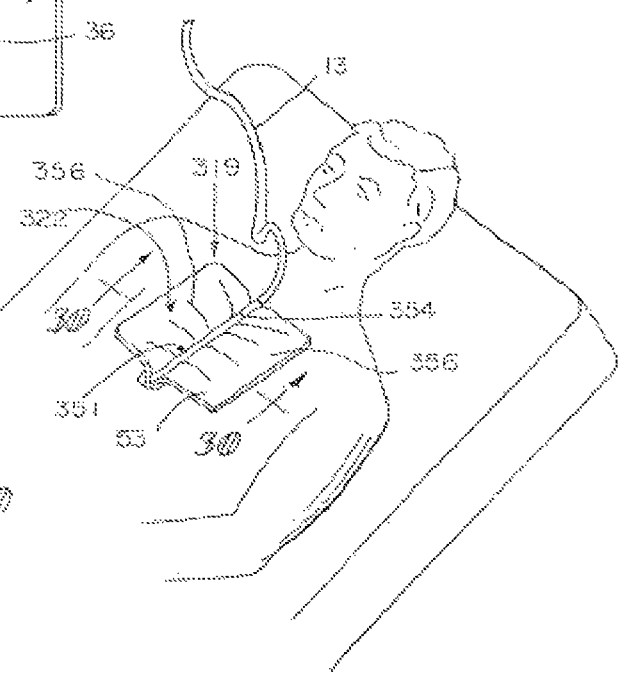
FIG. 29 is a perspective view of the V-shaped member of FIG. 28 showing the member on the sternal wound of a patient.
Figure 30:
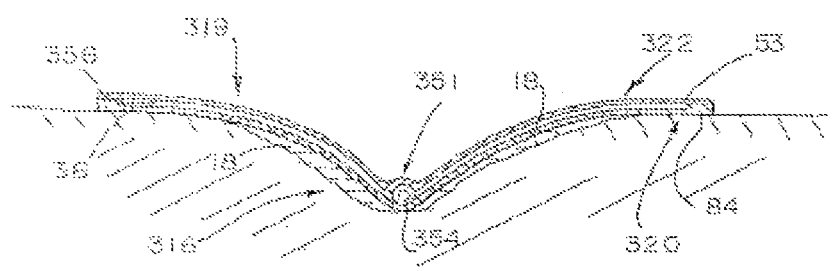
FIG. 30 is a sectional view taken along line 30-30 of FIG. 29 showing the V-shape of the member and also showing the wound contacting surface of the member adjacent the sternal wound surface.

Another illustrative member 319 is shown in FIGS. 28-30. Member 319 is provided for use with abdominal or sternal wounds 316. FIG. 29 shows member 319 being used to treat a sternal wound 316. As shown in FIGS. 29 and 30, member 319 is generally "V-shaped" and includes a right wing 350 and a left wing 352. Member 319 further includes a central portion 351 having a central passageway 354 and a port 340 coupled to tube 41 for communication with either vacuum source 12 or irrigation source 14. Right and left wings 350, 352 are each coupled to central portion 351. Lateral passageways 356 are formed by the cooperation of a wound contacting layer 320 and a cover 322 of member 319, as shown in FIG. 11. Lateral passageways 356 terminate before reaching the sides or peripheral edges of member 319. However, central passageway 354 is open at both a top and bottom edge of member 19. Through holes 36 are formed in wound contacting layer 320 and are provided for communication between passageways 354 and the wound surface 18. Although the communication between the wound surface 18 and the vacuum source 12 and/or irrigation source 14 is provided through central and lateral passageways 354, 356, as shown in FIG. 28, it is within the scope of this disclosure to provide a member 319 for use with abdominal and/or sternal wounds having a different passageway structure for communicating the vacuum source 12 with the wound surface 18. Further, although member 319 is V-shaped, it is within the scope of this disclosure to include a generally flat member which is flexible to adjust to the contour of the sternal or abdominal wound to which it is applied.

Figure 31:
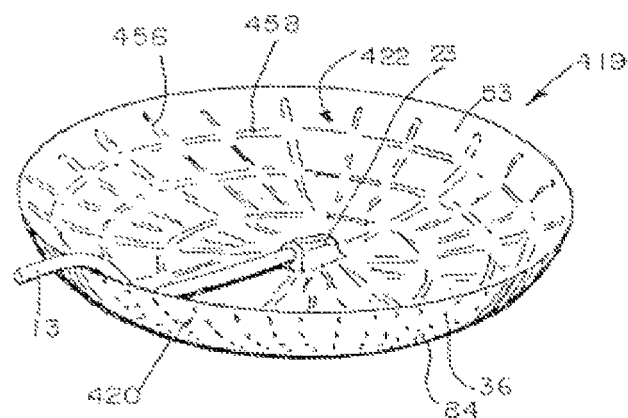
FIG. 31 is a perspective view of yet another embodiment of the member of the present invention showing the member being dome-shaped and having a convex wound contacting surface.

Yet another illustrative embodiment is shown in FIG. 31 where a generally dome-shaped member 419 is provided for use with deep wounds having a wound surface including side walls, for example. Dome-shaped member 419 is able to conform to side portions of a deeper wound bed, for example, to provide the side portions of the wound surface, as well as the bottom portion of the wound surface with suction and irrigation treatment. A port (not shown, but similar to port 51) is centrally located within member 419 and passageways 456 in communication with connecter 23 extend radially therefrom, as shown in FIG. 31. Concentric passageways 458 positioned around the port are also provided. Member 419 includes a cover 422 and a wound contacting layer 420 including a convex wound contacting surface 84 and through holes 36 in communication with passageways 456, 458. Wound contacting surface 84 is premolded to form the convex shape.

Figure 33:
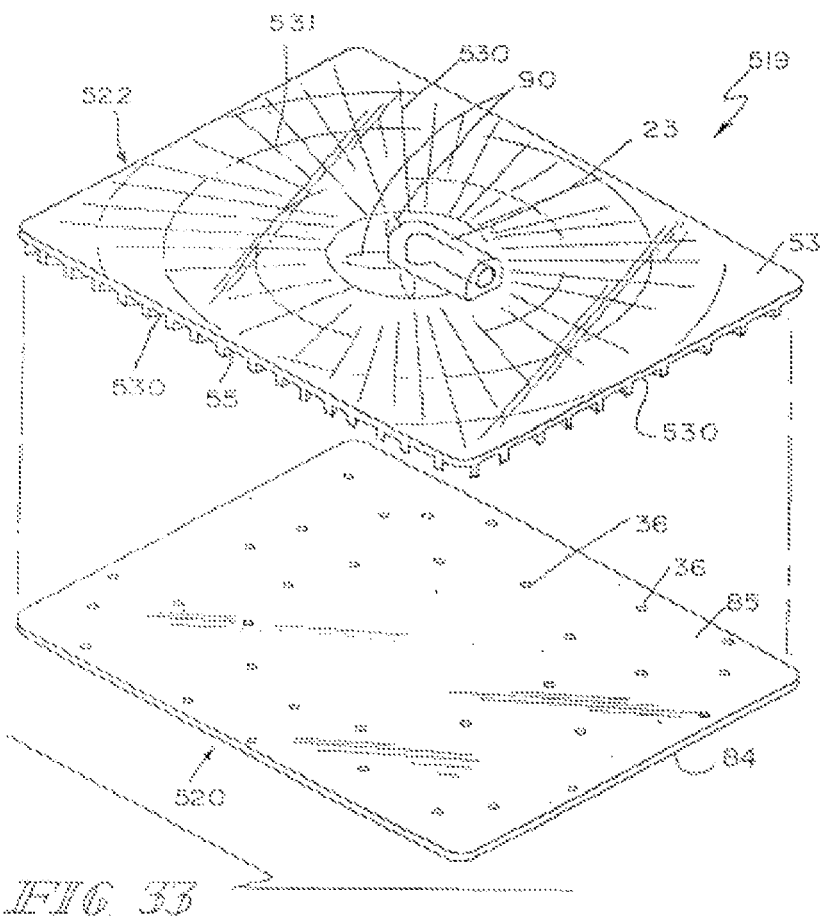
FIG. 33 is an exploded perspective view of another embodiment of the member showing a cover of the member having channels formed therein and also showing a wound contacting layer of the member having a smooth surface and thru holes for communication with the channels of the cover.
Figure 34:
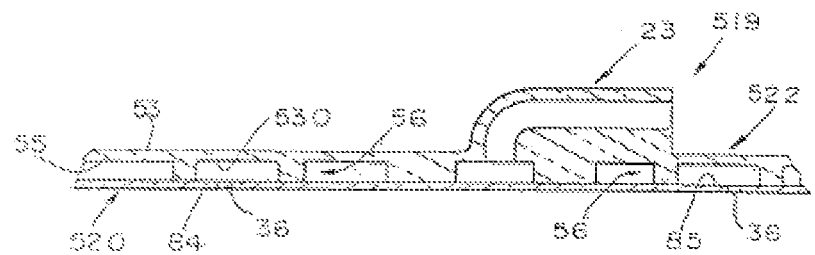
FIG. 34 is a sectional view of a portion of the member of FIG. 33.

As mentioned above and shown in FIGS. 17-22, member 19 includes a wound contacting layer 80 and a cover 52 coupled to the wound contacting layer 80 to form passageways 56. Passageways 56 are formed by the cooperation of layer 80 and cover 52. Specifically, passageways 56 are defined by the channels 28, 30 of layer 80 and the bottom surface 55 of cover 52 which covers and closes each channel 28, 30 to form passageways 56. It is within the scope of this disclosure, however, to form passageways 56 between a wound contacting layer 520 and a cover 522, as shown in FIG. 33, for example. A member 519, as shown in FIGS. 33 and 34, includes wound contacting layer 520 and cover 522 coupled to wound contacting layer 520. Connecter 23 is coupled to top surface 53 of cover 522 and is in communication with port 51 of cover 522. Cover 522 further includes a plurality of channels 530 radiating from port 51 and a plurality of concentric channels 531 formed around port 51. Further, cover 522 includes bosses 90 coupled to bottom surface 55.

Wound contacting layer 520 includes through holes 36. Opposite surface 85 of layer 520 is smooth such that passageways 562 are formed when layer 520 and cover 522 are coupled together. Effectively, member 19 and member 519 each include a port 51 in communication with vacuum source 12 and/or irrigation source 14, passageways 56 in communication with port 51 and connecter 23, and holes 36 in communication with passageways 56 and formed through wound contacting layers 80, 520. Member 19 and member 519 each further include bosses 90 to prevent port 51 from becoming sealed off by central area 87 when suction is applied to bandage 11. Bosses 90 provide an uncollapsable space in central area 87 between port 51 and passageways 56.

Members 19, 119, 219, 319, 419, and 519 discussed above are illustratively each provided for use with vacuum source 12 and irrigation source 14. As illustrated, these embodiments are provided with one port 51 for communication with either the vacuum source 12 or the irrigation source 14 or both. However, a member 616 is shown in FIGS. 35 and 36 and includes port 51, cover 52, layer 80 having a smooth or textured wound contacting surface 84, and an irrigation layer 650 coupled to surface 84 of layer 80. Irrigation layer 650 includes an irrigation port 652 for communication with irrigation source 14, as shown diagrammatically in FIG. 36. Irrigation layer 650 includes an upper surface 654 and a lower surface 656. As shown in FIG. 36, lower surface 656 is positioned to lie adjacent to the wound bed surface 18 and upper surface 654 is coupled to surface 84 of layer 80. As illustrated in this embodiment, layer 80 does not contact the wound bed surface 18; layer 80 acts as an intermediate layer positioned between cover 52 and irrigation layer 650. Irrigation layer 650 lies on the wound bed surface 18.

Further, irrigation layer 650 includes a plurality of channels 656 formed in upper surface 654 in communication with irrigation port 652 via a central channel 658 which is also formed in upper surface 654. Irrigation through holes 660 are formed in irrigation layer 650 and are positioned to lie within channels 656 and central channel 658. Fluid from irrigation source 14 flows through irrigation port 652 to central channel 658 and lateral channels 656, and finally flows through irrigation holes 660 to the wound bed surface 18, as shown in FIG. 36. Irrigation layer 650 further includes vacuum holes 662 positioned around channels 656, 658. Vacuum holes 662 communicate with the wound bed surface 18 and with through holes 36 of intermediate layer 80. Vacuum holes 662 do not directly communicate with channels 656, 658 of irrigation layer 650. Irrigation layer 650 is illustratively made from the same material as cover 52 and intermediate layer 80 such as silicone, for example.

Cover 52 and layer 80 are the same cover and layer 22, 80 as those shown in FIG. 17 and discussed above. Connecter 23 coupled to cover 52 is provided for communication with vacuum source 12. When cover 52, intermediate layer 80, and irrigation layer 650 are coupled together, as shown in FIG. 34, passageways 56 are formed between cover 52 and intermediate layer 80, as discussed above, and irrigation passageways 664 are formed between surface 84 of layer 80 and upper surface 654 of intermediate layer 650. Passageways 56 are in communication with vacuum source 12 while passageways 664 are in communication with irrigation source 14. As shown in FIG. 36, fluid flows into passageways 664 and out irrigation holes 660 to reach wound bed surface 18. This irrigation fluid and exudate from the wound surface 18 is then sucked up through vacuum holes 662 of irrigation layer 650 and through holes 36 of layer 80 to passageways 56 and finally out port 51 of cover 52. Member 619 allows simultaneous delivery of irrigation fluid to the wound surface 18 and application of suction to the wound bed surface 18 through separate and distinct passageways. Although the particular structure of member 619 is shown in FIGS. 35 and 36 and discussed above, it is within the scope of this disclosure to include any member having separate and distinct passageways for delivering fluid to and drawing a vacuum on the wound surface 18. It will be appreciated that, in some circumstances, the irrigation and suction may take place simultaneously.

Figure 37:
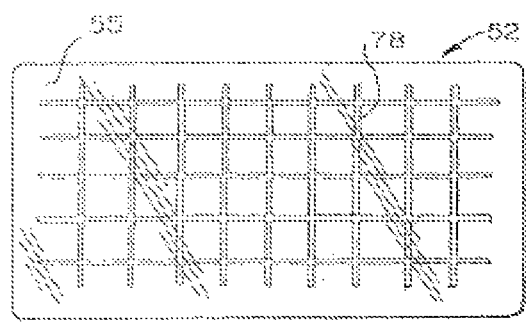
FIG. 37 is a bottom view of a cover showing a filament or wire form molded into the cover to allow the member to retain a desired shape when shaped or formed by a user or caregiver to fit a particular wound, for example.
Figure 38:
FIG. 38 is a sectional view of a member including the cover and wire form shown in FIG. 37.

Yet another illustrative member 719 is shown in FIGS. 37 and 38 including a wound contacting layer 80 and a cover 52 coupled to the layer 80. Member 719 further includes a filament or wire form 78 molded into the body of cover 52, as shown in FIG. 38, for example. Wire form 78 is provided to allow for a caregiver to mold member 719 into a desired shape, such as to the shape of the wound 16, for example. Member 719 will retain that shape due to the wire form 78 molded into the cover 52. Illustrative wire form 78 is a metal grid, as shown in FIG. 37; however, it is within the scope of this disclosure to include any type or configuration of a filament, fine screen, or wire form which retains its shape once formed to fit a particular shape as desired by the caregiver. Further, it is within the scope of this disclosure for the wire form 78 to be molded into either wound contacting layer 80 (or member 20) or cover 52 or both. Further it is within the scope of this disclosure to include wire form 78 molded into the cover and/or wound irrigation layer of any of the previously disclosed embodiments.

Figure 39:
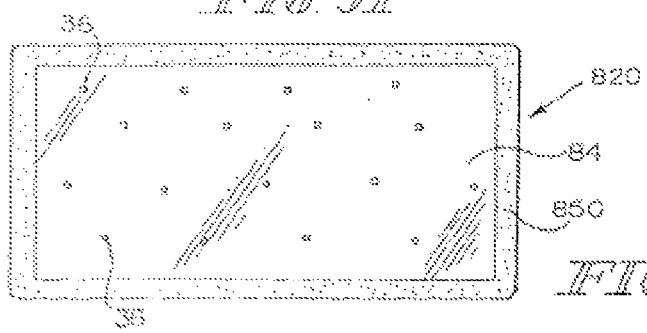
FIG. 39 is a bottom view of another member showing the wound contacting layer having an adhesive outer perimeter for sealing about the wound in order to provide a self-sealing member, as shown in FIG. 40.
Figure 40:
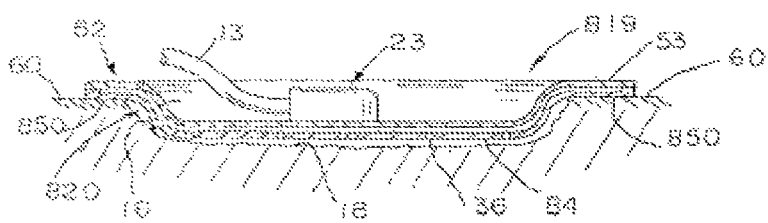
FIG. 40 is a sectional view of the member of FIG. 39 showing the outer adhesive perimeter of the wound contacting layer coupled to the patient's healthy skin surrounding the wound in order to seal the member about the wound without the use of the sealing film shown in FIG. 17.
Figure 42:
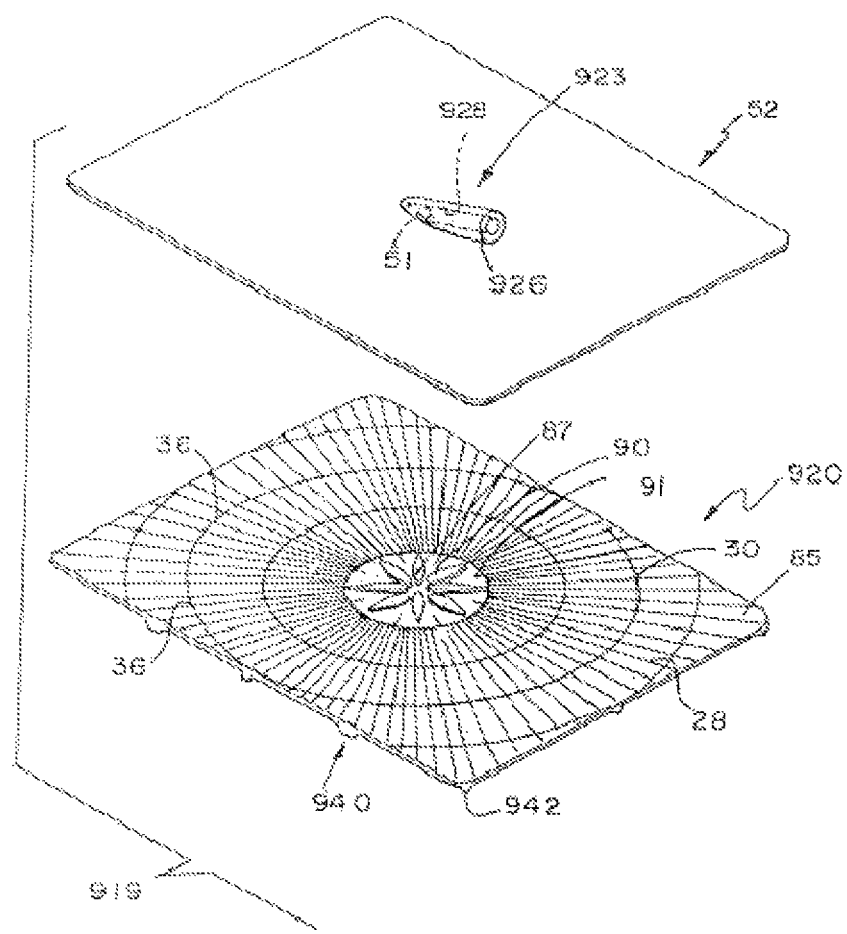
FIG. 42 is a perspective view of another member of the present invention showing a wound contacting layer, a cover, and a connector coupled to the cover of the member and also showing the connector having a single, angled passageway.
Figure 43:
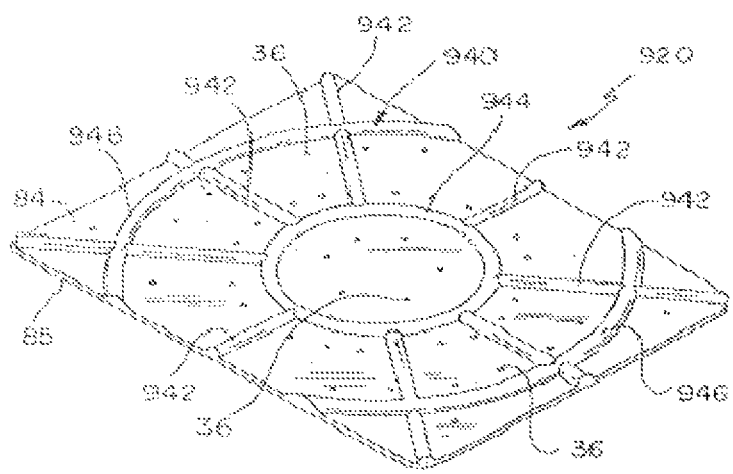
FIG. 43 is a bottom perspective view of the wound contacting layer of the member of FIG. 42 showing a single stand-off coupled to the wound contacting surface of the layer and generally forming a spider-web-like pattern having radially extending portions and concentric circular portions.
Figure 44:
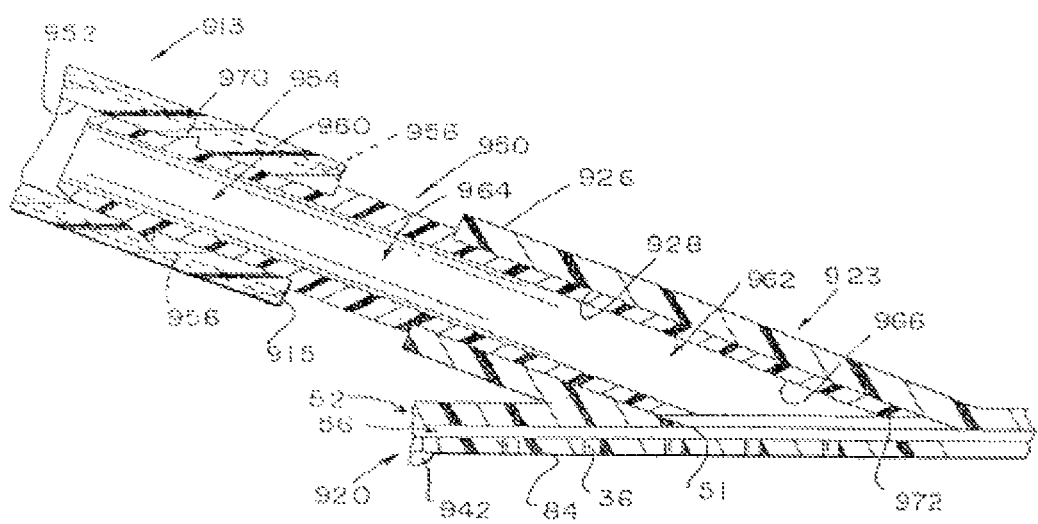
FIG. 44 is a sectional view showing the angled connector of the member of FIGS. 42 and 43 coupled to a multi-lumen tube by a barbed tube coupler.

Yet another illustrative member 819 is shown in FIGS. 39 and 40. A wound contacting layer 820 includes an adhesive 850 about the outer perimeter of wound contacting surface 84 of layer 820. As shown in FIG. 40, cover 52 is coupled to opposite surface 85 of layer 820 and connecter 23 is coupled to top surface 53 of cover 52. Adhesive 850 is provided to seal to the patient's healthy skin 60 surrounding wound 16. Adhesive 850, therefore, permits member 819 to be self-sealing such that a vacuum or negative pressure can be created above wound surface 18 without the use of sealing film 62. In order for adhesive 850 to be able to effectively seal to healthy skin 60, passageways 56 of member 819 are not formed to extend to the peripheral edges of member 819 unlike passageways 56 of member 19 which do extend to the peripheral edges of member 19. Although adhesive 850 is shown to be coupled to layer 820, it is within the scope of this disclosure to provide any member having an adhesive for attachment to the patient's healthy skin surrounding the wound so that the member is self-sealing and able to maintain a negative pressure above the wound without the use of a sealing film. For example, the wound contacting layer may be sized smaller than the cover and the bottom surface of the cover may include an outer adhesive perimeter for coupling with the patient's surrounding healthy skin. Yet another illustrative member 919 is shown in FIGS. 42-44. Member 919 is similar to the other members disclosed above and includes a wound contacting layer 920, cover 52 coupled to layer 920, and a connector 923 coupled to cover 52. As shown in FIGS. 42 and 44, connector 923 differs from connector 23 because connector 923 includes an outer wall 926 defining a single passageway 928 to port 51 of cover 52. Outer wall 926 and passageway 928 are positioned at an angle to top surface 53 of cover 52. In the illustrative embodiment, the included angle between an axis defined by passageway 928 and the top surface of cover 52, when cover 52 is in a flat configuration, is about 30 degrees.

It is understood that member 919 operates in the same or similar manner as the other members, such as members 19 and 20, described above. As such, the same reference numerals have been used to designate similar components to those components previously discussed and additional discussion thereof is not warranted.

One difference between member 919 and members 19 and 20 is that member 919 includes a single stand-off 940, shown in FIG. 43, which generally forms a spider-web-like pattern. Stand-off 940 is coupled to wound contacting or wound facing surface 84 and includes interconnecting portions or ridges including radial arms 942, circle portion 944, and arc portions 946 concentric with circle portion 944. Specifically, stand-off 940 includes eight radial arms 942 extending outwardly from circle portion 944 and through arc portions 946. It is within the scope of this disclosure, however, to include a stand-off having more circles portions and/or arc portions interconnected by more or less radial arms. Further, it is within the scope of this disclosure to include a stand-off forming other suitable interconnected patterns than that shown in FIG. 43. Although stand-off 940 includes radial arms 940, circle portion 944, and arc portions 946, the entire stand-off 940 is molded or formed as a single interconnected unit.

Stand-off 940 operates to position wound facing surface 84 of wound contacting layer 920 away from wound surface 18 of wound 16 (shown in FIGS. 3, 7, and 17). By positioning wound facing surface 84 away from wound surface 18, holes 36 (not visible in FIG. 42, but shown in FIGS. 43 and 44) of layer 920 are less likely to form an unwanted seal against wound surface 18. Stand-off 940 allows vacuum source 12 to establish a generally uniformly distributed negative pressure to draw exudate from the wound 16 through holes 36 and into channels 28, 30, of layer 920. Stand-off 940 is not provided to direct fluid flow toward any single hole 36, but instead, to prevent the holes 36 from becoming closed off and forming an unwanted seal against wound surface 18. As shown in FIG. 43, for example, stand-off 940 forms either fully or partially closed-off portions or encompassed regions of wound facing surface 84 defined by circle portion 944, radial arm portions 942, and arc portions 946. Each of the majority of the closed-off portions have multiple holes 36 associated therewith. Thus, each closed-off portion has portions of stand-off 940 fully or partially surrounding or encompassing associated holes 36.

Illustratively, the radial arms 930 and arc portions 934 of stand-off 940 extend to the outer peripheral edges of layer 920. It is within the scope of this disclosure, however, to include a stand-off having radial arms and/or arc portions which do not extend all the way to the outer peripheral edge of layer 920. Further illustratively, each radial arm 930, each arc portion 934, and circle portion 932 has a semi-circle shaped cross-section having a radius of about 0.0625 inches (1.588 mm).

As mentioned above, another difference between member 919 and members 19 and 20, for example, is that member 919 includes angled connector 923, as shown in FIGS. 42 and 44. Passageway 928 of connector 923 provides a generally straight flow path for the exudate removed from wound 12 through member 919 by vacuum source 12 and for the liquid delivered to wound 12 through member 19 by irrigation source 14.

As shown in FIG. 44, a barbed tube coupler 950 is provided to couple connector 23 with a multi-lumen vacuum/irrigation tube 913. Illustratively, tube 913 includes an inner lumen 952 defined by an outer wall 954 of the tube 913. Tube 913 further includes outer lumens 956 formed in outer wall 954. As shown in FIG. 44, inner lumen 952 is in communication with passageway 928 of connector 923 via the tube coupler 950 while outer lumens 956 are open to the area around member 919 through an end edge 915 of tube 913.

Barbed tube coupler 950 is received within inner lumen 952 and passageway 928. Coupler 950 includes a tube portion 960, a connector portion 962, an intermediate portion 964 coupled to and positioned between tube portion 960 and connector portion 962, and a passageway 966 through each of the tube portion 960, connector portion 962, and intermediate portion 964. Tube portion 960 is positioned within inner lumen 952 of tube 913 and includes a barb 970 to prevent tube portion 960 from being easily removable from tube 913. Connector portion 962 is press fit into connector 923 and includes an angled end 972 to generally engage and lie adjacent to cover 52. Intermediate portion 964 is positioned between and abuts each of the tube 913 and connector 923, as shown in FIG. 44. In some embodiments, adhesive or sealant is applied to either or both of portions 960, 962 to further enhance the connection between tube portion 960 of coupler 950 and tube 913 and between connector portion 962 of coupler 950 and connector 923.

Although this invention has been described in detail with reference to certain embodiments, variations and modifications exist within the scope and spirit of the invention as described and defined in the following claims.

What is claimed is:

1. A bandage for use with a vacuum source, the bandage comprising:

a flexible wound dressing member formed from a non-porous material and having a sheet-like configuration including a wound-facing surface and an opposite surface including a plurality of channels formed therein with a plurality of discrete holes extending from the channels through the wound dressing member; and a flexible cover having a sheet-like configuration and a port configured to be coupled to a vacuum source, the flexible cover coupled to the opposite surface to cover the plurality of channels and cooperate therewith to form passageways in fluid communication between the port and the plurality of holes in the wound dressing member;

wherein the bandage is configured so that the wound-facing surface can be disposed over a wound such that a vacuum source can be fluidly coupled to the port to apply negative pressure to the wound through the passageways and the holes.

2. The bandage of claim 1, where the wound dressing member has a perimeter, the cover has a perimeter, and the perimeter of the wound dressing member is coupled to the perimeter of the cover.

3. The bandage of claim 1, where the cover is generally non-porous.

4. The bandage of claim 1, where at least one of the wound dressing member and the cover is transparent.

5. The bandage of claim 1, further comprising:
a connector coupled to the cover and configured to coupled a vacuum source to the port.

6. The bandage of claim 1, further comprising:
a tube coupled to the port and configured to be coupled to a vacuum source.

7. The bandage of claim 1, further comprising:
an adhesive coupled to the wound dressing member and configured to coupled the wound dressing member to skin surrounding a wound.

8. The bandage of claim 1, further comprising:
a packing material adapted to cover the wound dressing member within the wound; and
a sealing film configured to cover the packing material and provide a sealed environment over the wound;
wherein the vacuum source is fluidly coupled to the bandage through the sealing film and the packing material to the port to apply negative pressure to the wound through the holes.

9. The bandage of claim 8, where the wound dressing member and cover are each non-porous.

10. The bandage of claim 8, where at least one of the wound dressing member and the cover is transparent.

11. The bandage of claim 8, where the packing material is porous.

12. The bandage of claim 8, further comprising:
a tube coupled to the cover and configured to be coupled to a vacuum source.

13. The bandage of claim 8, where the wound dressing member comprises a medical-grade material.

14. The bandage of claim 1, wherein the wound-facing surface has a plurality of channels formed therein with the holes extending between the channels of the wound-facing surface and the opposite surface.

15. The bandage of claim 1, wherein the wound-facing surface has a stand-off coupled to the wound-facing surface and configured to provide a space between the wound-facing surface and the surface of the wound.

16. The bandage of claim 1, wherein the wound-facing surface has a plurality of spacers coupled to the wound-facing surface and configured to provide a space between the wound-facing surface and the surface of the wound.

* * * * *